US009706910B1

(12) United States Patent
Blaha et al.

(10) Patent No.: US 9,706,910 B1
(45) Date of Patent: Jul. 18, 2017

(54) INTERACTIVE SYSTEM FOR VISION ASSESSMENT AND CORRECTION

(71) Applicant: Vivid Vision Inc., San Francisco, CA (US)

(72) Inventors: James J. Blaha, San Francisco, CA (US); Manish Gupta, San Francisco, CA (US)

(73) Assignee: Vivid Vision, Inc., San Francisco, CA (US)

( * ) Notice: Subject to any disclaimer, the term of this patent is extended or adjusted under 35 U.S.C. 154(b) by 0 days.

(21) Appl. No.: 14/726,264

(22) Filed: May 29, 2015

Related U.S. Application Data

(60) Provisional application No. 62/004,750, filed on May 29, 2014.

(51) Int. Cl.
*A61B 13/00* (2006.01)
*A61B 3/032* (2006.01)
*A61B 3/00* (2006.01)
*A61B 3/11* (2006.01)
*A61B 3/113* (2006.01)
*A61B 5/0205* (2006.01)
*A61B 5/021* (2006.01)
*A61B 5/024* (2006.01)
(Continued)

(52) U.S. Cl.
CPC .............. *A61B 3/032* (2013.01); *A61B 3/005* (2013.01); *A61B 3/0033* (2013.01); *A61B 3/111* (2013.01); *A61B 3/113* (2013.01); *A61B 5/02055* (2013.01); *A61B 5/021* (2013.01); *A61B 5/024* (2013.01); *A61B 5/0402* (2013.01); *A61B 5/0476* (2013.01); *A61B 5/0531* (2013.01); *A61B 5/0816* (2013.01); *A61B 5/11* (2013.01)

(58) Field of Classification Search
CPC ............ A61B 5/16; A61B 3/113; A61B 5/162
USPC ......................................................... 600/558
See application file for complete search history.

(56) References Cited

U.S. PATENT DOCUMENTS 5,910,834 A    6/1999   McClure et al.
8,057,036 B2   11/2011  Hess et al.
(Continued)

OTHER PUBLICATIONS

Aderman, Christopher M., et al. "Dichoptic virtual reality therapy for amblyopia in adults." *Investigative Ophthalmology & Visual Science*. 56.7 (2015): 2191-2191.
(Continued)

*Primary Examiner* — Daniel Cerioni
(74) *Attorney, Agent, or Firm* — Mintz Levin Cohn Ferris Glovsky and Popeo, P.C.

(57) ABSTRACT

Systems and methods for assessing vision and correcting vision problems are provided. A head-mountable virtual reality display controlled via a computing device can be worn by a user to display virtual reality images to the user. The images can be displayed as part of an interactive and engaging activity that can be used to determine a value of a certain parameter of the user's eyes. The activity can also be intended as a treatment procedure during which user's eyes are trained to perceive objects having certain properties that unassisted eyes of the user are normally not able to perceive. User input is acquired to determine user's perception of the displayed virtual reality images. The computing device can be a smartphone configured to perform the vision tests or treatment under control of a remote computing device operated by a trained clinician.

14 Claims, 20 Drawing Sheets

(51) Int. Cl.
    *A61B 5/053*     (2006.01)
    *A61B 5/0402*     (2006.01)
    *A61B 5/0476*     (2006.01)
    *A61B 5/08*     (2006.01)
    *A61B 5/11*     (2006.01)

(56) References Cited

U.S. PATENT DOCUMENTS

| | | |
|---|---|---|
| 8,066,372 B2 | 11/2011 | Cooperstock et al. |
| 8,454,166 B2 | 6/2013 | Fateh |
| 2006/0087618 A1 | 4/2006 | Smart et al. |
| 2013/0308099 A1* | 11/2013 | Stack ............ A61B 3/113 351/209 |
| 2014/0276130 A1* | 9/2014 | Mirelman ............ A61B 5/744 600/483 |
| 2015/0140529 A1* | 5/2015 | Tinjust ............ A61B 5/16 434/236 |

OTHER PUBLICATIONS

Blaha, J. and Gupta, M. "Diplopia: A Virtual Reality Game Designed to Help Amblyopics." Virtual Reality (VR), 2014 iEEE. IEEE, 2014.

Hess, R.F., et al. "An iPod treatment of amblyopia: An updated binocular approach." Optometry (St. Louis, Mo.) 83.2 (2012): 87-94.

Nordqvist, Joseph. "Tetris Video Game Helps Treat Lazy Eye." *Medical News Today*. MediLexicon, Intl., Apr. 23, 2013. Web. Aug. 18, 2015. <http://www.medicalnewstoday.com/articles/259547.php>.

Cooper, Jeffrey, "Computerized Vision Therapy for Home and Office Treatment of Accommodative and Vergence Disorders, and Amblyopia," Journal of Behavioral Optometry. 18(4): 88-93 (2007).

Waddingham et al., "Virtual Reality for Interactive Binocular Treatment of Amblyopia," Proc. 6th Intl Conf. Disability, Virtual Reality and Assoc. Tech., Esbjerg, Denmark. 201-208 (2006).

* cited by examiner

○ Tracked Object (Successfully Perceived by User)

◉ Tracked Object (Not Perceived by User)

○ Tracked Object (Successfully Perceived by User)

◉ Tracked Object (Not Perceived by User)

INTERACTIVE SYSTEM FOR VISION ASSESSMENT AND CORRECTION

CROSS REFERENCE

The present application claims priority to U.S. Provisional Application No. 62/004,750 entitled "VISION CORRECTION SYSTEM" filed May 29, 2014, which is hereby incorporated by reference in its entirety.

TECHNICAL FIELD

The subject matter described herein relates to a vision assessment and correction system including a computing device and a head-mountable virtual reality (VR) device communicatively coupled to the computing device.

BACKGROUND

Many people suffer from various vision disorders that are often left undiagnosed and untreated. Some visual problems affect a person since childhood, and, if not detected and treated in a timely manner, can result in a permanent loss of vision as the person gets older. For example, amblyopia, or "lazy eye," is a common visual disorder afflicting approximately 4% of the population in the United States. Amblyopia results from an incompatibility of visual perception between the brain and the amblyopic, "weak" eye, such that the other, "strong" eye, inhibits the amblyopic eye which results in a permanent decrease in vision in that eye. Amblyopia typically occurs in children, but adult cases occur as well.

A typical treatment for amblyopia involves the subject's wearing an eye patch over the unaffected eye with the goal of forcing the person to use the weaker eye to thus train that eye to become stronger. However, patients, particularly children, tend to view such treatment as inconvenient and uncomfortable, which results in poor compliance and therefore leads to unreliable results. Measuring a progress of such treatment can be challenging. Furthermore, a detection of amblyopia and other vision disorders in young children can be complicated.

SUMMARY

In one aspect, a computing system having at least one data processor and in communication with a head-mountable virtual reality display can be operated to display, using the at least one data processor and on the head-mountable virtual reality display, at least one first object having at least one property; receive, by at least one data processor, user input with respect to the at least one first object, the user input being generated based on input acquired from a user wearing the head-mountable virtual reality display; determine, by the at least one data processor using the received user input, that a target value of at least one parameter has not been reached, wherein the target value of the at least one parameter is indicative of a perception of the at least one property of the at least one first object by at least one eye of the user; and display, using the at least one data processer and on the head-mountable virtual reality display, when it is determined that the target value has not been reached, at least one second object having at least one property that is different from the at least one property of the at least one first object.

The at least one second object can include a modified representation of the at least one first object. The at least one first object and the at least one second object can be the same objects.

A representation of the at least first object can be removed, by the at least one data processor, from the head-mountable virtual reality display. The at least one first object can be displayed to evaluate at least one vision condition of the user. An indication of a selection of a test to evaluate the at least one vision condition of the user can be received, by at least one data processor.

It can be determined that the target value has been reached. When it is determined that the target value has been reached, a value of at least one parameter representative of a vision condition of the user can be identified.

It can be determined that the target value has been reached. When it is determined that the target value has been reached, a result can be provided. The result can be provided by displaying the result in a graphical user interface, storing the result in a storage device, loading the result into memory, or transmitting the result to a remote computing system.

The computing system can include a mobile computing device. Information displayed on the head-mountable virtual reality display can be controlled via a graphical user interface of a second computing device. The computing system can be configured to communicate with the second computing device via a remote connection.

The at least one first object can be displayed such that the at least one first object is visible to one of the left and right eyes of the user and is invisible to the other of the left and right eyes of the user. The at least one first object can also be displayed such that a first representation of the at least one first object is displayed for viewing by the right eye of the user and a second representation of the at least one first object that is different from the first representation is displayed for viewing by the left eye of the user.

Information relating to the displayed objects and to the received user input can be stored in a storage media.

The user input can include an instruction to display the at least one second object. The user input can be received using at least one sensor selected from the group consisting of at least one head tracking sensor, at least one eye tracking sensor, at least one gesture and motion recognition sensor, and at least one face and facial expression recognition sensor.

The at least one parameter can be selected from the group consisting of an angle of binocular disparity between images of the at least one object displayed to the left and right eyes, a ratio in contrast between a foreground and a background of the at least one object, an angular size of the at least one object, a position of the at least one object in a field of view, a brightness of the at least one object, an orientation of the at least one object, a depth of the at least one object, a length of time during which the at least one object is visible, and a speed of the at least one object.

In another aspect, the current subject matter can be implemented using a computing system including at least one data processor and in communication with a head-mountable virtual reality display. At least one first object having at least one property is displayed, using the at least one data processor. User input with respect to user's perception of the at least one first object is received, by the at least one data processor, the user input being generated based on input acquired from a user wearing the head-mountable virtual reality display. A plurality of second objects are iteratively presented to the user until it is determined that a perceptual target is reached, wherein at least some of the plurality of second objects are objects generated by modifying at least one property of the at least one first object, and wherein the perceptual target is determined based on the user input; and when it is determined that the perceptual target is reached, providing a result indicating a vision measurement or a visual disorder.

The user input can be received using at least one sensor selected from the group consisting of at least one head tracking sensor, at least one eye tracking sensor, at least one gesture recognition sensor, and at least one face and facial expression recognition sensor.

The result can be at least one selected from the group consisting of a measurement of a visual acuity, information relating to an improvement of a visual acuity, a measurement of perception of movement, a determination of a visual field, a determination of at least one blind spot, a determination of color perception, and a measurement of contrast sensitivity. The result can also be at least one selected from the group consisting of a determination of depth perception, an identification of a dominant eye, information relating to breaking suppression of an amblyopic eye, a measurement of an interpuppilary distance, information relating to strengthening a weak eye.

In yet another aspect, a computer system for vision assessment and correction includes a computing device comprising at least one data processor and at least one computer-readable storage medium storing computer-executable instructions, and a head-mountable virtual reality device configured to communicate with the computing device and having a virtual reality display configured to render a virtual reality environment. The at least one data processor can be configured to execute the computer-executable instructions to perform: displaying, using the at least one data processer and on the virtual reality display, the virtual reality environment comprising at least one first object having at least one property; receiving, by at least one data processor, user input with respect to the at least one first object, the user input being generated based on input acquired from a user wearing the head-mountable virtual reality display; determining, by the at least one data processor using the received user input, that a target value of at least one parameter has not been reached, wherein the target value of the at least one parameter is indicative of a perception of the at least one property of the at least one first object by at least one eye of the user; and displaying, using the at least one data processer and on the virtual reality display, when it is determined that the target value has not been reached, at least one second object having at least one property that is different from the at least one property of the at least one first object.

The at least one second object can be a modified representation of the at least one first object.

The user input can be received from at least one input device selected from the group consisting of a mouse, a keyboard, a gesture and motion tracking device, a microphone, at least one camera, an omnidirectional treadmill, and a game pad. The user input can also be received from at least one sensor selected from the group consisting of a head tracking sensor, a face tracking sensor, a hand tracking sensor, an eye tracking sensor, a body tracking sensor, a voice recognition sensor, a heart rate sensor, a skin capacitance sensor, an electrocardiogram sensor, a brain activity sensor, a geolocation sensor, at least one retinal camera, a balance tracking sensor, a body temperature sensor, a blood pressure monitor, and a respiratory rate monitor.

The computing system can be a mobile computing device. Information displayed by the head-mountable virtual reality device can be controlled via a second computing device.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g., the Internet, a wireless wide area network, a local area network, a wide area network, a wired network, or the like), via a direct connection between one or more of the multiple computing systems, etc.

The subject matter described herein provides many technical advantages. The visual activities are delivered to users in an interactive and engaging manner such that the users are more inclined to perform tests and treatments for extended periods of time and with frequency that can be required to achieve adequate results. The activities can be in the form of a game which can be appropriate for different ages. Thus, young children for whom early detection of visual abnormalities is often critical for correction of the abnormalities before the onset of adolescence are more likely to engage in the activities. The compliance issues typically exacerbating standard visual correction techniques, such as wearing an eye patch to correct amblyopia, can therefore be alleviated. Thus, the subject matter improves overall experience of a user during assessment of user's visual conditions and treatment of visual disorders.

The described system can use a variety of computing devices, such as, for example, any suitable mobile device. The VR device worn by a user during an activity allows controlling brightness and other image parameters such that tests and treatments can be delivering in a controllable and reproducible manner. In this way, user's performance can be assessed and monitored in a more reliable manner. The head-mountable VR device can be any type of a VR device, which can include a low-cost device. Thus, the tests and treatments can be available for a large proportion of a population. Furthermore, the virtual environment delivered to the user by the VR device can be controlled via a remote computing device which can be operated by a trained clinician. In this way, users located in rural and other geographically distant areas can receive proper vision care.

The details of one or more variations of the subject matter described herein are set forth in the accompanying drawings and the description below. Other features and advantages of the subject matter described herein will be apparent from the description and drawings, and from the claims.

DETAILED DESCRIPTION

Certain exemplary aspects of the current subject matter will now be described to provide an overall understanding of the principles of the systems and methods disclosed herein. One or more examples of these aspects are illustrated in the accompanying drawings. Those skilled in the art will understand that the systems and methods specifically described herein and illustrated in the accompanying drawings are non-limiting exemplary aspects and that the scope of the aspects is defined solely by the claims. Further, the features illustrated or described in connection with one exemplary aspect may be combined with the features of other aspects. Such modifications and variations are intended to be included within the scope of the described subject matter.

The current subject matter provides methods, systems, and computer program products to detect, assess and treat vision disorders in subjects. The system can include a computing device configured to communicate with a head-mountable virtual reality (VR) device that creates a virtual reality environment for a user wearing the VR device such that a display, or screen, is positioned over the user's eyes. The VR device includes at least one data processor, a visual interface, and memory storing instructions for execution by the at least one data processor. The VR device allows displaying images to the user in a controlled and reproducible manner. The computing device controls the VR device to display various images such that the user can perform an activity in the form of a vision test or vision correction treatment procedure. The activity can be interactive and engaging, such as a game, and the user can therefore be more inclined to perform the activity for duration of time sufficient to achieve desired results. User input can be acquired with respect to the displayed images, in response to user's operation of an input device or by using sensors monitoring movement of user's eye, head, hands, or other body parts. The displayed images can be modified based on the user input in a manner that allows receiving progressively better test or treatment results. The computing device can be automated or controlled by a clinician that can operate a remote computing device, which allows treating patients at geographically distant locations from the clinician.

Figure 1:
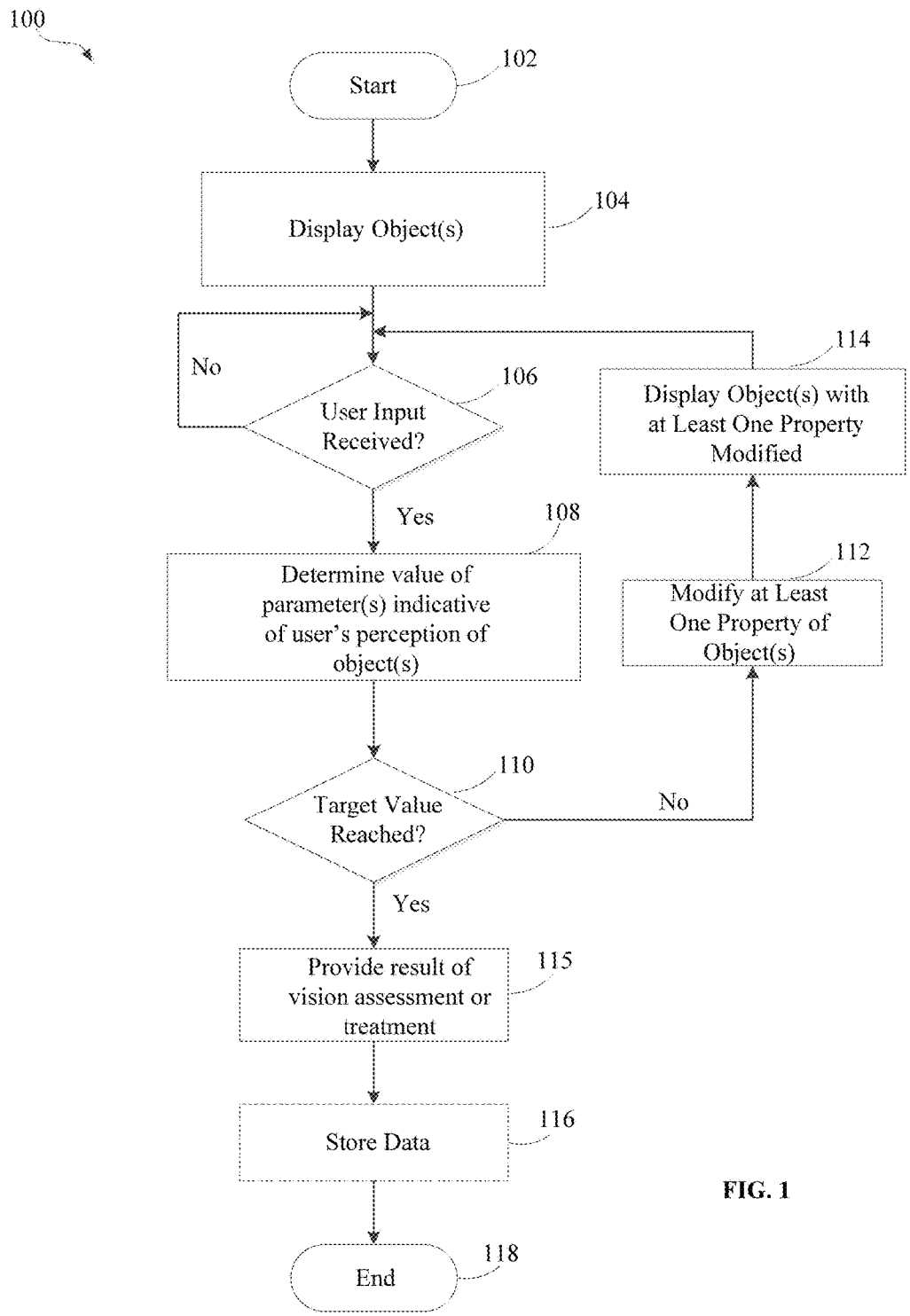
FIG. 1 is a flowchart illustrating a process of executing an activity to test user's vision or treat a vision problem.

FIG. 1 is a process flow diagram 100 illustrating a method of operating a computing system to assess and/or treat a vision disorder of a person. The computing system can include at least one data processor and memory communicatively coupled to the at least data processor. The memory can be configured to store computer-executable instructions embodied as a vision correction platform or application. The computer-executable instructions, when executed by the at least one data processor, perform the described method. Furthermore, in some aspects, the entire or part of the platform can be stored on a remote computing device and can be accessible via the computing device. The computing system is in communication with a head-mountable virtual reality (VR) display, as discussed in more detail below.

As shown in FIG. 1, the process 100 can start at block 102, at any suitable time. The process 100 can start upon a trigger, such as a user input. For example, the process 100 can start when the platform stored in the memory of or accessible via the computing device receives instructions to initiate and a user provides identification information required to execute the platform. The user can be a patient, a parent of a patient, or other person. In some implementations of the current subject matter, the process 100 can start in response to a user input received from an ophthalmologist, optometrist, or a vision therapist. The user, or patient, whose vision is to be assessed or corrected, is wearing the head-mountable virtual reality (VR) display. The user himself or herself can control initiation, progress, and termination of the process 100 via the computing device and various input devices. Furthermore, in some aspects, the ophthalmologist or other person can control information presented to the user on the VR device. Depending on a type and intended results of a test or treatment procedure being conducted, which is referred to herein as "the current activity," and type(s) of the object(s) being displayed on the VR device, some or all features of the process 100 can be controlled automatically, without user input.

The process 100 can start when the current activity is selected from a number of activities that can be performed using, for example, a platform implementing the current techniques. For example, as discussed in more detail below in connection with FIG. 3, the platform can present the user which a plurality of activities available to the user and the user can select an activity to be performed and option(s) associated with the activity. The activity can also be suggested to the user (e.g., automatically selected), for example, based on user's overall progress, user's performance of other activities, and other factors. The activity can also be selected by medical personnel, such as a clinician operating a computing device controlling the execution of the platform.

Regardless of the way in which the process 100 is started, at block 104, an image including a representation of at least one object, referred to herein as the "at least one object" for brevity, is displayed on the VR device. The image to be viewed by the user can be displayed such that, in reality, different images are displayed to the left and right eyes of the user. Thus, the at least one object can be displayed such that a first representation of the at least one first object is displayed for viewing by the right eye of the user and a second representation of the at least one first object that is different from the first representation is displayed for viewing by the left eye of the user. In some aspects, the at least one object can be displayed such that a representation of that object is visible to one of the left and right eyes of the user and is invisible to the other of the left and right eyes of the user. In other aspects, the object can be displayed to both eyes but with the color, brightness, contrast, or other properties different between the two eyes.

The at least one object can be selected from a variety of different objects, depending on the current test or treatment procedure performed using the process 100. The at least one object can have a plurality of properties, such as a shape, size, contrast, color (including color mixtures), texture, position on the display (e.g., within a scene), movement pattern, movement speed, depth (binocular disparity), time during which the object is displayed, etc. The objects can be various geometric shapes, objects resembling real life objects, abstract objects, text, and any combination thereof. The object can be displayed against a 3D background, which can also have various properties, such as a color, texture, contrast, depth, and other properties.

Subsequently, at block 106, it can be determined whether a user input with respect to the at least one object has been received. The current activity can require that a user input is received with respect to one or more properties of the displayed object. For example, the object may need to be moved, selected, looked at, and manipulated in any other manner. The user can indicate in a number of ways whether the user was able to perceive the object and one or more of its properties, or a relationship between the object and other displayed objects.

The user input can be acquired via a suitable input device configured to be operated by the user. For example, the input device can be a three-dimensional input device. Furthermore, additionally or alternatively, the user input, such as movement of the user's head, can be acquired via the VR device. The VR device can also be configured to track movements of the user's eyes, such that the VR device can acquire movement of the user's eyes as part of the user input. The user input can include voice, textual input which can be acquired based on a typed, pronounced or otherwise received text. The described system can also be equipped with gesture-recognition sensors such that no input device can be required and the user input can be received based on movements of the user's hand(s), head, and/or movements of the user's entire body. Additionally, at least one face and facial expression recognition sensor can be employed.

If the user input has not been received, the process 100 can return to block 106 to continue executing until the user input is received. It should be appreciated that, in some implementations of the current subject matter, at least one object can be presented to the user such that no user input is required. In such cases, the user can be instructed to simply view the VR device for a certain amount of time. However, the process 100 requires that user input is received with respect to the objects displayed to the user wearing the VR device.

If it has been determined, at block 106, that the user input has been received, the process 100 branches to block 108 where it is determined, by the at least one data processor, using the received user input, a value of parameter(s) indicative of a perception of the at least one property of the at least one first object by one or both eyes of the user. The one or more parameters indicative of the perception of the at least one property of the displayed objects can be parameters representing a manner in which the user perceives the object displayed on the display of the VR device. Non-limiting examples of parameters include an angle of binocular disparity between images of a virtual object being displayed to each eye, a ratio in contrast between the foreground and background of the object, an angular size of the object, an object's position in its field of view, an object's brightness, an orientation of the object, a depth of the object, a length of time the object was visible to the user, and the speed of the object.

It is then determined, at decision block 110, whether the target value of the one or more parameters has been reached. The determined value of the one or more parameters can be compared to the target value to determine whether the target value has been reached. The target value can be a value that depends on a particular goal of the current activity. The target value can be a numerical value of one or more parameters at which the activity is determined to be completed. For example, the target value can be a value of the one or more parameters indicating a size, position, and distance to the objects at which the user no longer can tell the objects apart, the user can no longer see the object, or the user can barely see the object. The target value can be a value of the one or more parameters that is determined to be statistically significant. This can be done using, for example, a p-value or a confidence interval.

In one example, an activity intended to conduct a stereo acuity test involves displaying two objects of different binocular disparities that have the same angular size and shape. The user is instructed to select an object perceived by the user as having a larger disparity, using binocular vision. After a user input indicating a selection of one of the displayed objects is received, the disparity is modified by being increased or decreased, using, for example, a staircase algorithm. A p-value can be calculated for the measurement, and the target value can be determined to be reached if the calculated p-value is below a certain threshold (e.g., $p<0.01$). Alternatively, the target value can be determined to be reached if it is determined that a lower or upper limit for disparity has been reached.

It should be appreciated that, in some aspects, the process 100 can execute until a certain number of iterations is performed. Also, the process 100 can execute for certain duration of time. Some treatments are required to be performed a number of times, for example, 20 minutes a day several times a week for one month.

If it is determined, at decision block 110, that the target value has not been reached, the process 100 branches to block 112 where at least one property of the at least one displayed object can be modified. The at least one object can be modified in a number of ways, which can include modification of the object and/or a scene behind or around the object. Non-limiting examples of parameters that can be modified include lighting, contrast, brightness, texture, color, size, position, rotation, saturation, speed of movement, speed of appearance, pattern of motion, direction of motion, speed of rotation, and other parameters. The object can be modified such that a resulting modified object is a different object, meaning that an alternative object with different properties can be displayed after the modification. The object can also be modified, as in many of the activities, such as the modified object resembles the object before the modification, but one or more of the visual properties are different. The properties can be modified by different degrees, which can be done incrementally or randomly. For example, in some activities, a value of a property can be decreased or increased with small increments.

The at least one property of the at least one object displayed on the display of the VR device can be modified automatically such that no user input is needed to be received to modify the at least one property. Furthermore, in some aspects, additional user input can be required to modify the at least one property. For example, the user performing the activity can provide input to modify one or more properties of the displayed objects. Also, a clinician or other person controlling operation of the computing device can modify one or more properties of the displayed objects.

It should be appreciated that, in some aspects, at least one property of the at least one object displayed on the display of the VR device can be modified a number of times, and appropriate user input can be acquired each time the property is modified. After sufficient amount of information relating to the user's performance of the activity is thus acquired, a value of one or more parameters indicative of the user's perception of the object can then be determined and compared to a target value.

The object with one or more properties modified can be then displayed, at block 114. The process 100 then returns to decision block 106, to determine whether user input with respect to the at least one modified object is received. The process 100 can be executed in two or more iterations such that an image presented to the user via the display of the head-mountable VR device is modified in some manner at each iteration of the process 100. In this way, the process 100 can be executed so as to train the user's eyes to perceive certain properties of the displayed objects and to successively improve user's vision.

Alternatively, if it is determined, at decision block 110, that the target value has been reached, the process 100 continues to block 115 where a result of the process can be provided, as shown in FIG. 1. As mentioned above, the process 100 can be a vision assessment procedure or a treatment intended to improve a vision condition of a user. The result can include one or more values of acquired measurements, values representing information on user's performance acquired during the activity. The result can be in any suitable format, such as a textual, graphical, audio, visual, any combination thereof, and any other format.

The result can be provided in a number of ways. For example, it can be displayed on a graphical user interface, which can be a graphical user interface of the user's computing device (e.g., computing device 202 in FIG. 2) or a graphical user interface of any other computing device. In some cases, the result can be provided using a display of the VR device. The result can also be provided by storing the result in a storage device, loading the result into memory, or transmitting the result to a remote computing system. The remote computing system can be, for example, a server or other computing system configured to store information acquired during the process. The remote computing system can also be a computing device operated by a clinician or other medical professional who can communicate with the user and can control, at least in part, the process 100 via the remote computing system. The remote computing system can be any other computing system.

As shown in FIG. 1, the process 100 can then follow to block 116 where data acquired in connection with the current activity can optionally be stored, or logged. The data can include the type of the current activity, type(s) of object(s) being displayed and their properties, timing of the activity, user actions, timing of the user actions, and any other information. It should be appreciated that any information relating to the current activity can also be logged as the activity is being performed. For example, information acquired during each iteration of the activity can be logged. The stored information can be accessed at a later time, as discussed below.

When the target value is reached, a result of the activity executed as the process 400 can be provided. The resulting vision measurement, information relating to a user's vision condition, or other information can be displayed or otherwise provided to the user or other person (e.g., a clinician). The result can depend on whether the activity was a test or a treatment, or whether it had elements of both a test and treatment. If the activity was a test assessing or diagnosing a user's condition, the result can include measurements of the user's vision such as, for example, user's strabismic deviation, visual acuity, stereo acuity, user's perception of movement, contrast sensitivity, a location of the blind spots, and a field of view. The result can also include identification and degree of binocular vision disorders, such as a measurement of a depth perception, a dominant eye, suppression of a weak eye, interpupillary distance, etc. If the activity was a treatment, the result can include information about the treatment or other suitable information. If the activity was a treatment that also involved elements of a test (e.g., breaking suppression, improving acuity, improving color sensitivity, improving stereo acuity, strengthening a weak eye and training the brain to use the weak eye, etc.), the result can include duration of time during which the treatment was conducted, measurements of user's progress during the activity and as compared to that user's prior performance (and/or as compared to performance of the same or similar activity by other users), and any other information.

As shown in FIG. 1, the process 100 can then end, at block 118. The process 100 can end when the current activity is determined to be completed or upon a trigger, such as user input. Furthermore, the process 100 can be a continuous process such that another activity can be selected and new types of object(s) can be displayed at block 104.

Figure 2:
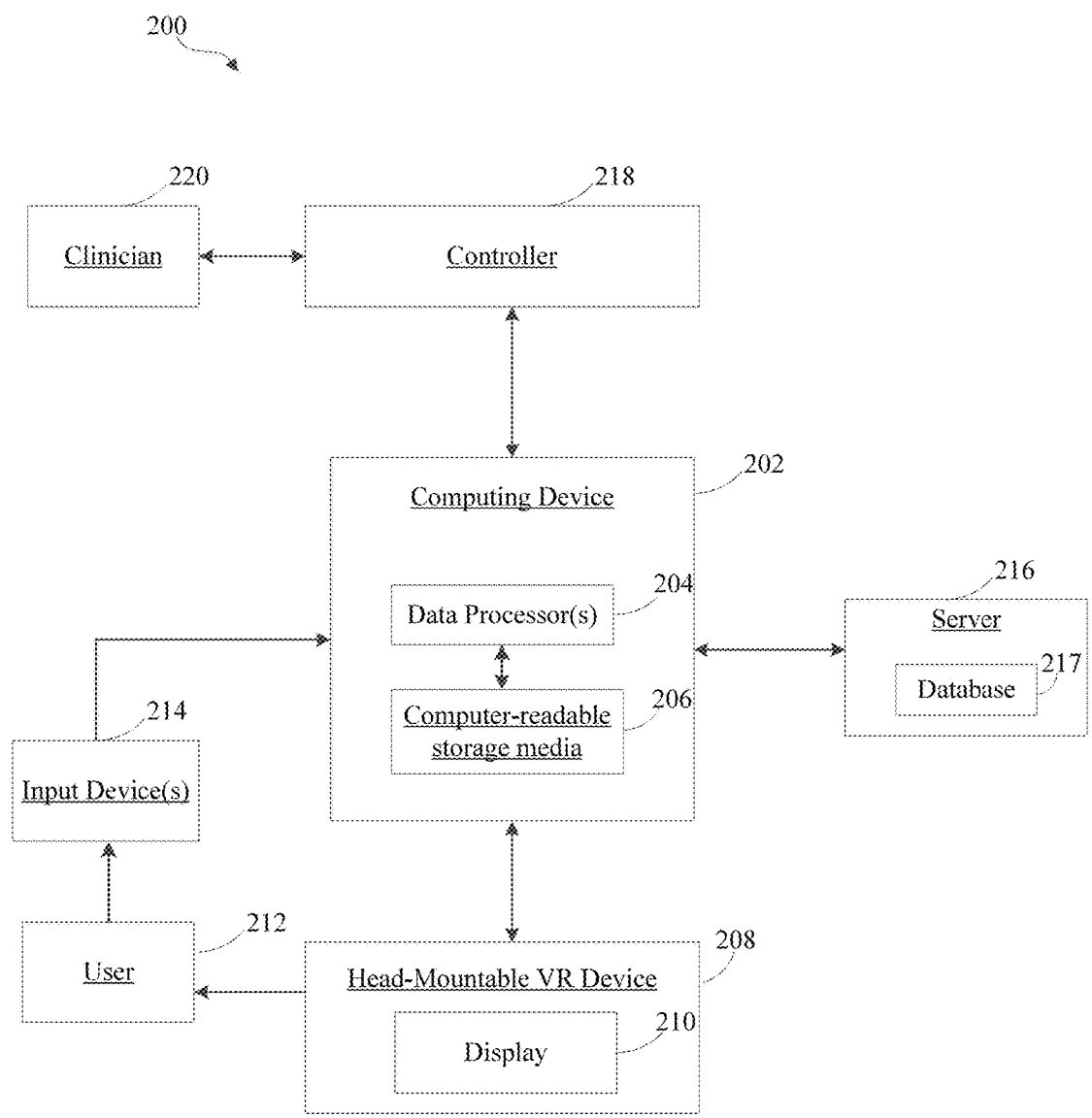
FIG. 2 is a block diagram illustrating a computer system in which the process of FIG. 1 can be implemented.

FIG. 2 illustrates a computer system 200 which can be configured to perform a process of diagnosing, assessing or treating a vision disorder afflicting a user 212, such as, for example, the process 100 of FIG. 1. The user 212 can be any person that can be a child or an adult. The system 200 includes a computing device 202 including at least one data processor 204 and computer-readable storage media 206 coupled to the at least one data processor 204. The system 200 also includes a head-mountable virtual reality (VR) device 208 configured to communicate with the computing device 202 and having a display 210 configured to display virtual reality images to a user 212 wearing the VR device 208 such that the display is disposed in front of the user's eyes. As shown in FIG. 2, the system 200 can also include one or more input device 214 configured to acquire user input based on active input received from user 212 and/or based on passively acquired sensor image data. Information acquired by the one or more input devices 214 is transmitted to the computing device 202, as shown in FIG. 2.

As also shown in FIG. 2, the computer system 200 can include or it can communicate via a remote connection with a server 216 which can include one or more databases 217 stored on one or more storage media and configured to store information acquired by the computing device 202 and other computing devices. The information, at least in part, can also be stored in the memory 206 of the computing device.

As further shown in FIG. 2, the computer system 200 can also include a controller 218, such as, for example, a touch display coupled to the computing device 202 and configured to receive user input from a clinician 220 or other type of input for controlling operation of the computing device 202 and the VR device 208 in connection with diagnosing, assessing or treating a vision disorder afflicting the user 212.

The computing device 202 can be any suitable computing device, such as a desktop or laptop personal computer, a personal digital assistant (PDA), a smart mobile phone, a server, or any other suitable computing device that can be operated by a user and can present services to a user. As mentioned above, the computing device 202 includes the at least one data processor 204 and the one or more computer-readable storage media 206. Computer-executable instructions implementing the techniques described herein can be encoded on one or more computer-readable storage media 206 to provide functionality to the storage media. These media include magnetic media such as a hard disk drive, optical media such as a Compact Disk (CD) or a Digital Versatile Disk (DVD), a persistent or non-persistent solid-state memory (e.g., Flash memory, Magnetic RAM, etc.), or any other suitable storage media. It should be appreciated that, as used herein, a "computer-readable media," including "computer-readable storage media," refers to tangible storage media having at least one physical property that may be altered in some way during a process of recording data thereon. For example, a magnetization state of a portion of a physical structure of a computer-readable medium may be altered during a recording process.

The computing device 202 can be coupled to the VR device 208 via a wired or wireless connection. Similarly, the computing device 202 can be coupled to the controller 218 via a wired or wireless connection.

The head-mountable VR device 208 can be any suitable wearable device configured to provide a virtual reality or holographic reality space to the user 212 of that device 208. The VR device 208 includes at least one data processor, a visual interface such that the display 210, and computer-readable storage media for storing computer-executable instructions for execution by the at least one data processor. In some aspects, portions of the display of the VR device 208 can be transparent, semi-transparent, or opaque. The VR device 208 can be a holographic computing device having a see-through holographic display. For example, the VR device can be a HoloLens device developed by Microsoft Corporation. The VR device can be in the form of smart glasses or it can have other configuration.

The display 210 of the VR device 208 can display a different video image to each eye of the use thus providing the user a sense of depth and 3D vision. The VR device 208 can be configured to use a head tracking technology such that the device 208 acquires and transmits to the computing device 202 information about the position and/or rotation of the head of the user 212. The display 210 can also be configured to implement eye tracking technology, which allows the VR device 208 to provide to the computing device 202 information about the position, xy location, rotation, and pupil size indicating pupil dilation of the user's eyes.

The VR device 208 provides certain advantages to the described techniques of assessing and treating vision problems. Thus, as compared to, for example, VR projectors, the VR device 208 provides a VR visual environment that gives a user a more realistic feeling of being part of such environment and a larger field of view where an accurate control of the image being shown to each eye can be achieved. Furthermore, when a user is wearing the head-mountable VR device 208, brightness can be a more controllable parameter since the VR device 208 itself provides a source of light to the displayed images. Other parameters of the displayed images are also more controllable thus allowing generating more consistent results, which can be particularly advantageous for reproducibility of the activities performed by the user and comparison of performance results for the same user or among multiple users.

As mentioned above, the VR device 208 can acquire and transmit to the computing device 202 input in the form of information on user's eye movement and/or information on user's head movement. The user input can also be acquired based on the user's using one or more input devices 214 communicatively coupled to the computing device 202. Non-limiting examples of the input device 214 include a mouse, keyboard, gesture/motion tracking device, microphone, camera(s), omnidirectional treadmill, game pad, body temperature monitor, pulse rate monitor, blood pressure monitor, respiratory rate monitor, electroencephalography device, or any other device.

The computing device 202 and the VR device 208 can be used in a home setting or other environment outside of a medical facility. Thus, the computing device 202 coupled to the VR device 208 can be controlled by the user 212 operating the devices. It should be understood that, if the user 212 is a young child who needs assistance with operating the devices, a parent or other person can assist such user.

In some aspects, the computing device 202 and the VR device 208 can be employed in a clinical setting such as in a suitable medical facility. In such scenarios, operation of the computing device 202 can be controlled via the controller 218 which can be, e.g. a touchscreen device coupled to the computing device 202 and operated by a clinician 220. The touchscreen device can mirror images visible to the user 212 via the VR display 210 (e.g., images for the left and right eyes of the user 212) and it can be configured so as to receive input for controlling the virtual environment images displayed on the VR display 210. The controller 218 can be a monitor or a computing device similar to the computing device 202, or any other device. Regardless of the particular type of the controller 218, a display associated with the controller 218 can be used to control in real time, as the user 212 is wearing the VR device 208, the virtual environment provided to the user 212.

In some aspects, the controller 218 can communicate with the computing device 202 wirelessly over a computing network including wireless communication medium or media for exchanging data between two or more computers, such as the Internet. The controller 218 can thus be located at any location assessable via the computing network, including a location geographically remote from a location of the computing device 202. Thus, a user equipped with the computing device 202, such as a mobile phone (e.g., a smartphone or any hand-held computing device which can be a convergent device encompassing capabilities of multiple devices), and a suitable VR device 208 (which can be a low-cost headset as known in the art or developed in the future) can be located remotely from a clinician operating the controller 218 to control via the computing device 202 the virtual environment of the user. This telemedicine technique can simplify, decrease costs of, and make more accessible early diagnosis and timely treatment of many vision disorders. Because communication between trained medical professionals and patients is simplified and fewer or no hospital visits can be required, more patients can receive access to proper treatment of vision problems. The telemedicine approach can be particularly advantageous for persons living in rural, remote locations where such persons would otherwise have limited access to adequate vision care.

As shown in FIG. 2, the computing device 202 can communicate with the server 216 over a communication network, such as the Internet. The server 216 acts as a central repository of data relating to vision treatment platforms (e.g., a platform performing the process 100 of FIG. 1) executed on a plurality of computing devices including the computing device 202. Data relating to all measurements and treatments conducted using the described techniques, including timing data, can be recorded and stored on the database 217 in the server 216, which can be one or more databases. The users can then view a complete history of their visual performance. The data stored on the server 216 can be accessible to the user via a computing device, such as the computing device 202 or any other device, in a manner that allows the user to sort and analyze the historical data in various ways, view various statistics derived from the data, compare that user's performance to the performance of other users (e.g., based on averages generated from all of the users, or any other parameters). The results of the analysis and comparison can be presented to the user or other person (e.g., a clinician) in visual formats that facilitate understanding of the results. The user can be enabled to customize the manner of the representation of the results.

As mentioned above, the process 100 (FIG. 1) can be implemented as a platform embodied as computer-executable instructions stored on the computer-readable storage media 206 of the computing device 202 and executed by the at least one data processor 204 of the computing device 202. The computer-executable instructions, when executed by at least one data processor, perform the described vision assessment and correction techniques. Thus, the process 100 of FIG. 1 can be performed under control of computer-executable instructions embodying the platform, although the described techniques are not limited to the specific mechanism by which the process is controlled. The computer-executable instructions can additionally or alternatively be stored on any other computing device, and the platform can be accessible via the computing device 202.

Figure 3:
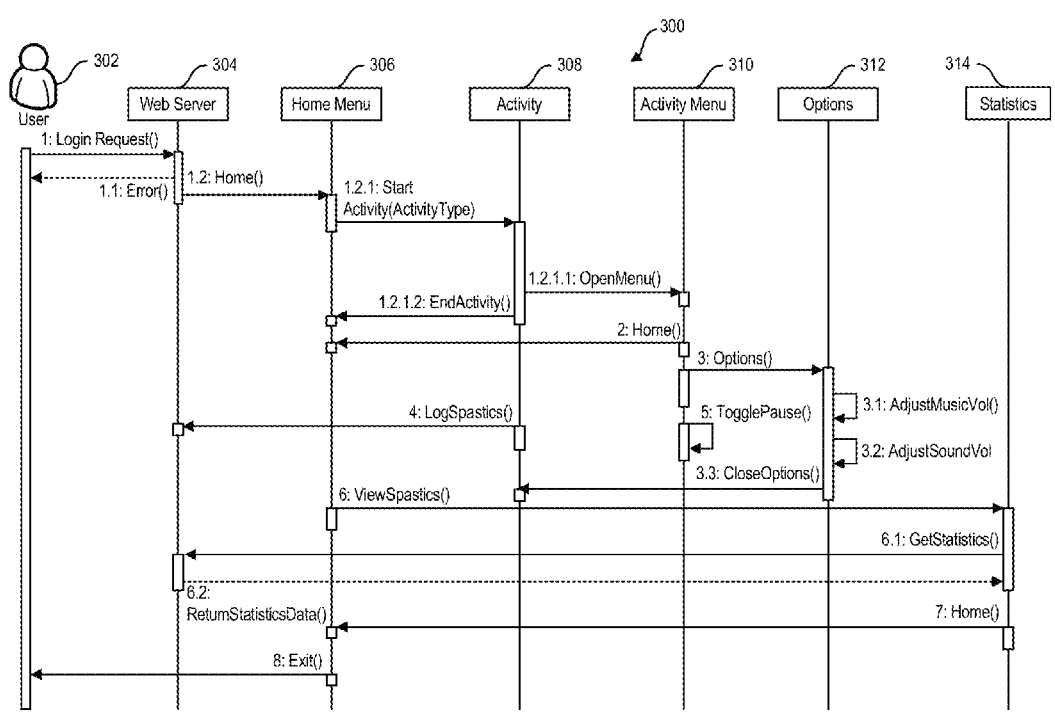
FIG. 3 is a schematic diagram illustrating a process of interaction of a user with a platform implementing the process of FIG. 1.

Regardless of the way in which the platform is implemented and controlled, a user can register with the platform or a clinician or other person can register the user. For example, a user profile including identification information about the user, user's medical history and any other information can be stored, for example, on the server 216. FIG. 3 shows a schematic diagram 300 illustrating a process of interaction of the user with the platform. The interaction with the platform can occur via a suitable computing device such as the computing device 202.

As shown in FIG. 3, in a home or other setting outside a medical facility, when the platform is initiated by the user 302 (e.g., user 212 in FIG. 2), the user can be prompted to provide authentication information to log in. After the login is authenticated by a web server 304 (e.g., the server 216 in FIG. 2), a home menu 306 can be presented to the user enabling the user to select a test/treatment, various options, and/or statistics. For example, the platform can present to the user various activities such that the user can select an activity 308. The user can select the activity 308 upon which an activity menu 310 can be displayed that allows the user to select various options 312 relating to a test or treatment implemented as the activity 308, such as adjusting a music or sound volume, or adjusting any other parameters. After the activity 308 is selected based on the user input, a 3D scene appropriate (e.g., a virtual and holographic scene) for that selected test or treatment can be rendered to the user wearing a VR device, such as the VR device 208 (FIG. 2), on her or his head.

Any pertinent data acquired during the activity and any determined measurements can be transmitted for storage to a database on the web server 304. After the activity 308 is completed, statistics information 314 can be presented to the user which can be navigated through the home menu 306. In this way, the user can view his or her activity history, the calculated measurements, and any other data collected during the latest and all prior activities performed by this user and/or other users. It should be appreciated that, although the user can be enabled to compare his or her performance to that of other users, the identity of other users can remain anonymous. Alternatively, the activity can be implemented as a multiplayer game in which case the participating users are aware of each other's identities and performance. As shown in FIG. 3, the user can exit the platform by selecting an exit option from the home menu 306.

In some aspects, the platform can be controlled by a clinician, e.g., via a touchscreen device such as controller 218 of FIG. 1. The clinician can be any appropriately trained medical professional. In such cases, the clinician can be prompted to log in. When the login completes successfully, a graphical user interface (GUI) can be presented that allows the clinician to view and update information on patients and tests and treatments performed by the patients. The clinician can view, add, edit, archive, and select patient-related information. The controller 218 can enable the clinician to communicate with one or more patients via respective computing devices operated by the patients or other people (e.g., patient's parents). Thus, the GUI rendered on the display of the controller 218 can enable the clinician to select a patient along multiple patients and to control test or treatment to be performed by the selected patient.

Once the patient, or user, is selected, a virtual environment to be presented to that user is loaded on the user's head-mountable VR device and it is also mirrored to the display (e.g., a touch screen monitor) of the controller 218 operated by the clinician. The GUI presented to the clinician can include various features that can be configured to receive user input to thus allow controlling information presented to the patient. Information presented to one or both of the left eye and the right eye of the patient can be displayed on the controller 218, along with the features that allow controlling the information presented to one or both of the eyes. The features can include, for example, three buttons which allow controlling the virtual environment of the user to "cover" the left eye, "cover" the right eye, or to view information presented to both eyes at the same time.

The clinician can use the GUI to select tests or games which are loaded into the virtual environment of the patient. Also, various settings can be selected which change various properties of the virtual environment. The controller 218 can allow the clinician to communicate with and control the virtual environments of more than one patient simultaneously. The clinician can also transmit to the patients various help information, to update and post blog posts, and perform other suitable actions related to testing and treating patients at various, including remote, locations.

The vision correction techniques described herein can involve rendering an image, or a scene, provided to each eye of the user in order to assess or treat vision problems. The scene can include one or more objects each having a plurality of properties. Different information can be presented to each eye. The information can be presented to the user in an interactive manner, requiring user input to control some of the elements in the scene. The scene can be a 3D scene presented to the user such that some objects in the scene are visible only to the left eye, only to the right eye, or both eyes. In some cases where the same object(s) are shown to both eyes, those objects can be presented such that different representations are rendered to the left and right eyes. The differences between the representations can include but not limited to, for example, some combination of lighting, contrast, brightness, texture, color, size, position, rotation, saturation, and speed on a per-eye basis. Additionally or alternatively, various aspects of the cameras of the VR device which render the scene to each eye can also be changed, including but not limited to a change in a field of view, brightness, blur, translation, and rotation.

In some implementations of the current subject matter, activities can follow a similar logic while different types of objects can be displayed and different properties of the objects can be altered as part of a particular activity. Each activity to be performed by the user can be implemented to be used as a test or treatment. The test is intended to diagnose a certain condition or determine absence thereof and measure related parameters of one or both eyes of the user. The treatment is intended to correct a vision disorder. It should be appreciated that some activities can incorporate elements of both test and treatment.

Figure 4:
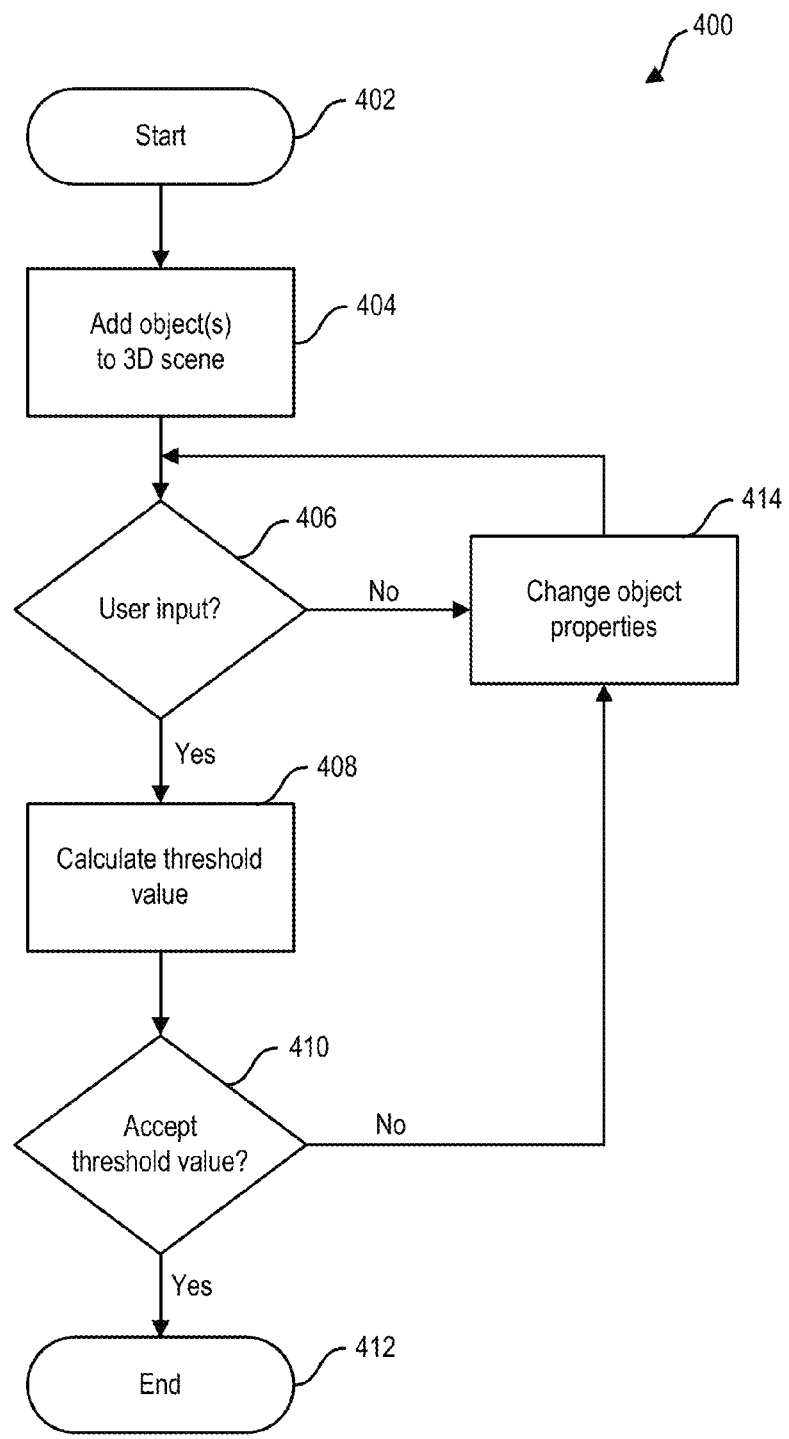
FIG. 4 is a flowchart illustrating a process of executing an activity.

FIG. 4 illustrates a process 400 of executing an activity that involves requesting user input relating to modifying one or more properties of objects in a scene, for one or both of the eyes of the user and for one or both of cameras of a VR device, until a certain perceptual goal is reached.

In general, the process 400 can be similar to the process 100 of FIG. 1. However, the process 400 can require that user input including a confirmation that the perceptual goal has been reached is received. As shown in FIG. 400, after the process 400 is started at block 402 in a suitable manner, one or more object(s) having at least one property can be added to the 3D scene, at block 404. If it is then determined at decision block 406 that relevant user input is received, the process 400 can branch to block 408 where a threshold estimate is determined based on a value of the at least one property of the object being displayed. The process 400 then includes determining, at decision block 410, whether the determined threshold estimate is within a desired confidence interval. Other measures of the accuracy of the threshold estimate can also be used. If it is determined, at decision block 410, that the threshold estimate is within a desired confidence interval and is therefore acceptable, the process 400 can then end at block 412. Although not shown in FIG. 4, it should be appreciated that any data acquired during execution of the process 400, including the determined threshold estimate, can be stored for future use.

However, if the determined threshold estimate is not acceptable, the process 400 can return to block 414 where the at least one property of one or more of the displayed objects is modified and such modified object is displayed to the user. The at least one property can be modified automatically or based upon user input instructing the platform to modify the property. Thus, at each iteration of the process 400, over time, the at least one property of the object(s) in the scene is modified, as information displayed to one or both of the eyes and/or information controlling one or both of the left and right cameras. At each iteration of the process 400, the intensity (or value) of one or more properties can be modified such that it is increased or decreased, until user input is received confirming that the user perceives the object in accordance with the goal of the activity. Furthermore, during some activities, the at least one property of the object(s) can be changed randomly such that the values of the property are modified until the user input is received indicating that the user perceived the object(s) in accordance with the goal of the activity. As another variation, some activities involve automatically determining whether to change the one or more properties randomly or based on respective user input.

As mentioned above, the process 400 can require an affirmative input that the perceptual goal has been reached. For example, the user input can indicate that the user performed the activity, viewed, appropriately perceived a property of, moved or otherwise manipulated the object as desired in accordance with the activity's goal(s). If it is determined at decision block 406 that the user input is not received, which can indicate that the user was not able to appropriately perform a required task, such as to perceive the object, the at least one property of one or more of the displayed objects can be modified at block 414 and the modified object is displayed to the user. The process 400 then continues to block 406 to monitor whether the user input is received.

Figure 5:
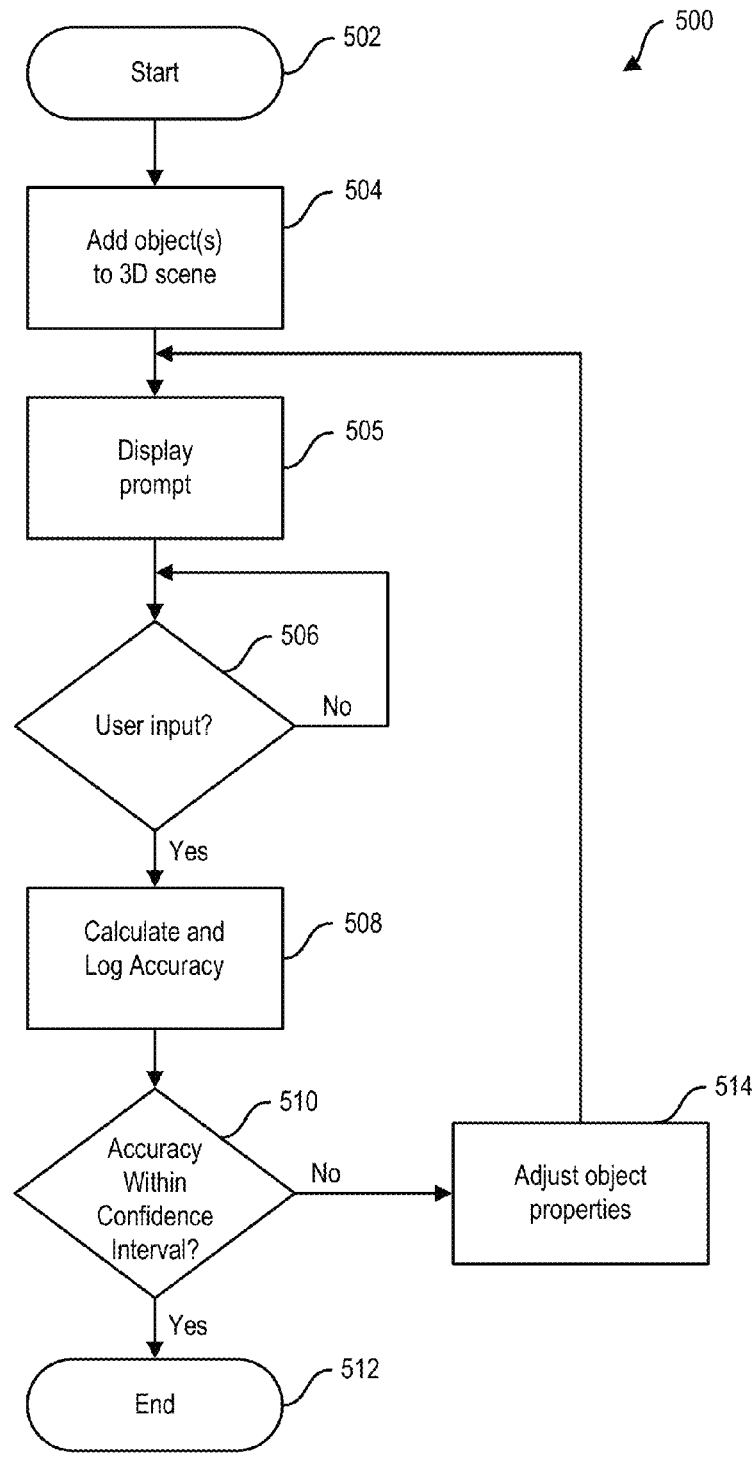
FIG. 5 is another flowchart illustrating a process of executing an activity.

Some activities require that user input is acquired with respect to user's making a selection of an option from two or more options presented to the user. The question can include an instruction to select an option, e.g., to select one of the objects being displayed. FIG. 5 illustrates an exemplary process 500 for performing such an activity. Thus, after the process 500 is initiated at block 502, two or more objects can be added to the 3D scene, at block 504. One or more properties of the displayed objects are different. For example, the two objects can have different binocular disparities, contrast against the background, brightness, color, orientation, motion, rotation, scale, or texture. At block 505, a prompt can be presented to the user requesting the user to select one of the objects. For example, the user can be presented with a question about which objects the user thinks has specific values for one, or a range, of the object's' properties. The user can be prompted with a relevant question in a suitable format, such as a textual, audio or any combination thereof. In some cases, the question can be presented as a cue, as part of an interactive game. For example, when the activity is intended for a user such as a small child, the objects can be displayed in a manner that can help the user to realize what action is desired.

If it is then determined at decision block 506 that the user input indicating the user's choice with respect to the displayed objects is received, the process 500 can branch to block 508 where a value of an accuracy of the user's selection is determined and related information is stored (logged) on a web server (e.g., server 216 of FIG. 2). The process 500 includes determining, at decision block 510, whether the determined accuracy value is within a desired confidence interval. If it is determined, at decision block 510, that the accuracy value is within a desired confidence interval and is therefore acceptable, the process 500 can then end at block 512. It should be appreciated that any data acquired during execution of the process 500 can be stored for future use. If the determined accuracy value is not within the desired confidence interval, the process 500 can follow to block 514 where the at least one property of one or more of the displayed objects is modified and such modified object is displayed to the user. As shown in FIG. 5, the process 500 then continues to block 505 where the prompt to the user is displayed. The prompt can be the same as the previously displayed prompt such that the user can be trained to recognize a difference in the same or similar property among the objects, or it can be a different prompt. Thus, the process 500 can execute until the accuracy value is determined to be within a set confidence interval. Such accuracy value is logged to the web server.

If it is determined at decision block 506 that the user input is not received, the process 500 can loop back to block 506 to monitor whether the user input is received.

Figure 6:
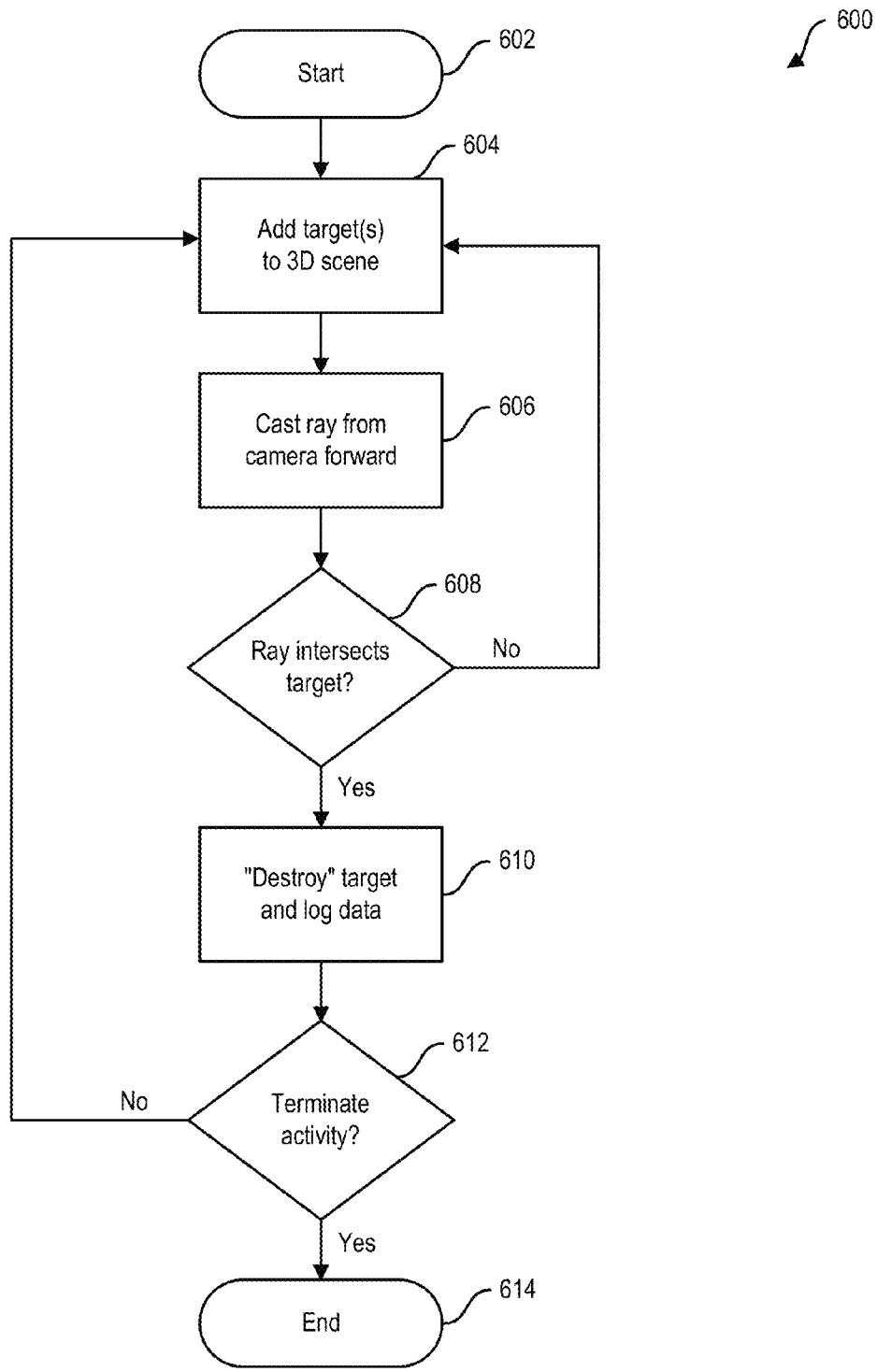
FIG. 6 is another flowchart illustrating a process of executing an activity.

Some activities require detecting whether a user can perceive objects under certain conditions. For example, FIG. 6 illustrates a process 600 that, after it is started at block 602, includes displaying at least one object, referred to as a target, at block 604. A single object can be displayed at a time. Alternatively, two or more object can be displayed, each object having at least one property that is different from properties of the other objects. The objects with different visual properties can be displayed at various locations of the scene (e.g., a 3D scene) presented to the user.

In the example of FIG. 6, user input is received indicating that the user looked at the object upon which the object is "destroyed." In other words, the object that the user looked at is removed from the scene such that it is no longer visible. As shown in FIG. 6, after the target objects are displayed at block 604, it is determined at whether input indicating the user viewed the target is acquired. This determination can involve tracking eye movements of the user using a VR device worn by the user during the activity. Thus, the VR device can cast a ray forward, at block 606, and it can be determined, at block 608, whether the ray intersects the displayed target. If the ray does not intersect the displayed target, the process 600 can return to block 606 where the ray is casted. However, if it is determined, at block 608, that the ray intersects the displayed target indicating that the user viewed the target, the target can be "destroyed"—ceased to be displayed at block 610. It should be appreciated that the event of user's viewing the displayed object can be detected in other ways. For example, movements of the user's head can be tracked and certain head positions can be taken as an indication that the user looked at the object. Other suitable approaches can be used additionally or alternatively.

Information related to the "destroyed" object can be stored. The information can include a type of the object, its properties, its position, a time at which it was displayed, a time at which it was "destroyed," and any other suitable information.

Subsequently, it can be determined, at block 612, whether sufficient amount of data has been acquired such that the current activity can terminate. The amount of data that can be determined to be sufficient can be an amount of data, such as measurements related to user's performance, that can be used to determine that the acquired results are reliable. If it is determined that the sufficient amount of data has been acquired, the process 600 can end. Alternatively, if it is determined that the amount of acquired data is not sufficient, the process 600 can return to block 604 where another object or multiple objects are displayed to the user. The process 600 can thus be repeated with different object properties until enough data is collected.

The described techniques include activities that require that the user confirms the perception of certain objects while the user's gaze remains fixed. Objects with different visual properties can be displayed in various locations of the scene, or a single object can be displayed at a time. User input can be received indicating that the user can perceive the displayed object, upon which the object is "destroyed." As in the example above, acquired data relating to the activity can be stored. The process then repeats with different object properties until sufficient amount of data is collected.

The described techniques also include activities implemented as games. For example, activities including tests or treatments which take a longer time to complete to achieve a desired result (e.g., more than a few minutes), can be more effective in the form of games. The games can be interactive and engaging such that a user's performance is rewarded with achievements, points, trophies, and other rewards. Thus, the user can be more inclined to perform the activity for an extended duration of time. A vision problem treatment can therefore be delivered to the user in a more effective manner.

An activity can include delivering appropriate visual information to a user and sensors. Sensors can be used to measure a user's reaction to the visual information. The sensors can include one or more of head tracking, eye tracking, voice recognition, heart rate, skin capacitance, EKG, brain activity sensors such as EEG, hand and body tracking, geolocation, retinal cameras, balance tracking, temperature, and pupil tracking and any other types of sensors.

In some aspects, an activity can require that a virtual visual field of one or both eyes is modified either entirely or in part. This involves processing the image after the scene has been rendered but before the scene has been displayed to the viewer.

A VR device used to create a virtual reality environment presented to a user of the VR device can be any suitable device. A conventional VR device accessible for many potential users can be a low resolution, low-cost device.

However, some of the tests and treatments can require high resolution optics for desired results. Thus, a custom designed set of optics can be used to convert a low resolution VR display into a high resolution display. The optics can include a pair of lenses, a convex lens and a concave lens, to "minify" the image (make it smaller than the original), and focus the image near optical infinity. The custom optics can be used to replace the optics of an off-the shelf VR display before administering tests which require a certain resolution, e.g., a 70 pixels/degree resolution or higher. The conventional optics can then be placed back in the VR display if subsequent activities do not require high resolution optics.

Figure 7:
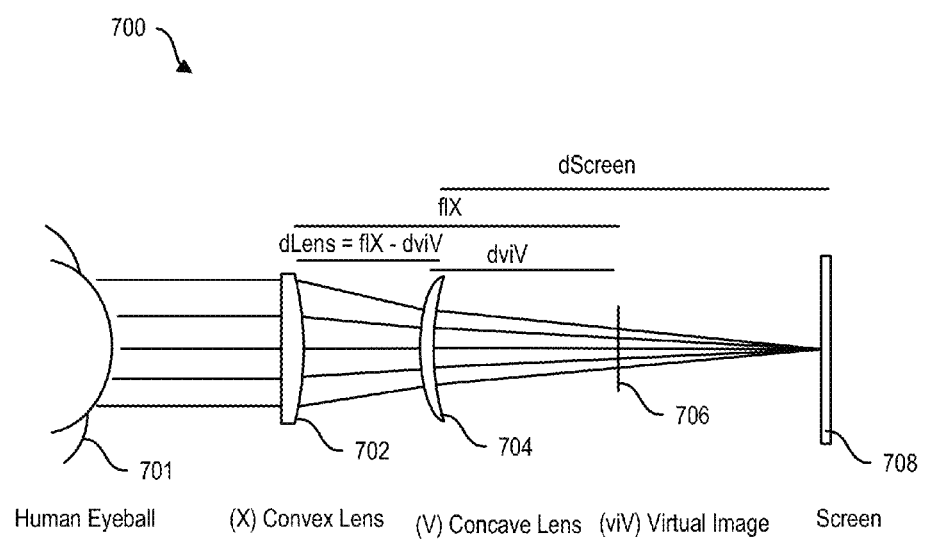
FIG. 7 is a schematic diagram illustrating an optical system for a VR display that allows the display to achieve higher resolution.

FIG. 7 illustrates an optical system 700 for a VR display that allows the display to achieve high resolution. The system 700 can be used to achieve a desired angular resolution and a total size of the lens. As shown in FIG. 7, the system 700 includes a convex lens (X) 702, a concave lens (V) 704, a virtual image (viV) 706 and a screen 708 configured to display the virtual image 706 to be viewed by a human eyeball 701. In FIG. 7, flX is a focal length of the convex lens (X) 702, flV is a focal length of the concave lens (V) 704, dLens is a distance between the convex and concave lenses 702, 704, dScreen is a distance between the concave lens (V) 704 and screen 708, and dvlV is a distance from lens concave lens (V) 704 to the virtual (viV) 706.

The techniques described herein can be used to treat various vision disorders and assess a condition of the user's eyes. The non-limiting examples below describe disorders and conditions that can be assessed and treated using the described systems and methods. It should be appreciated that the tests and treatments described below can be performed via any suitable activity that can be performed similarly to process 100 (FIG. 1), process 400 (FIG. 4), process 500 (FIG. 5), process 600 (FIG. 6), or using a modification or combination of the processes 100, 400, 500, and 600, or using any other process.

Binocular Vision Disorders

Measuring Depth Perception

Figure 8A:
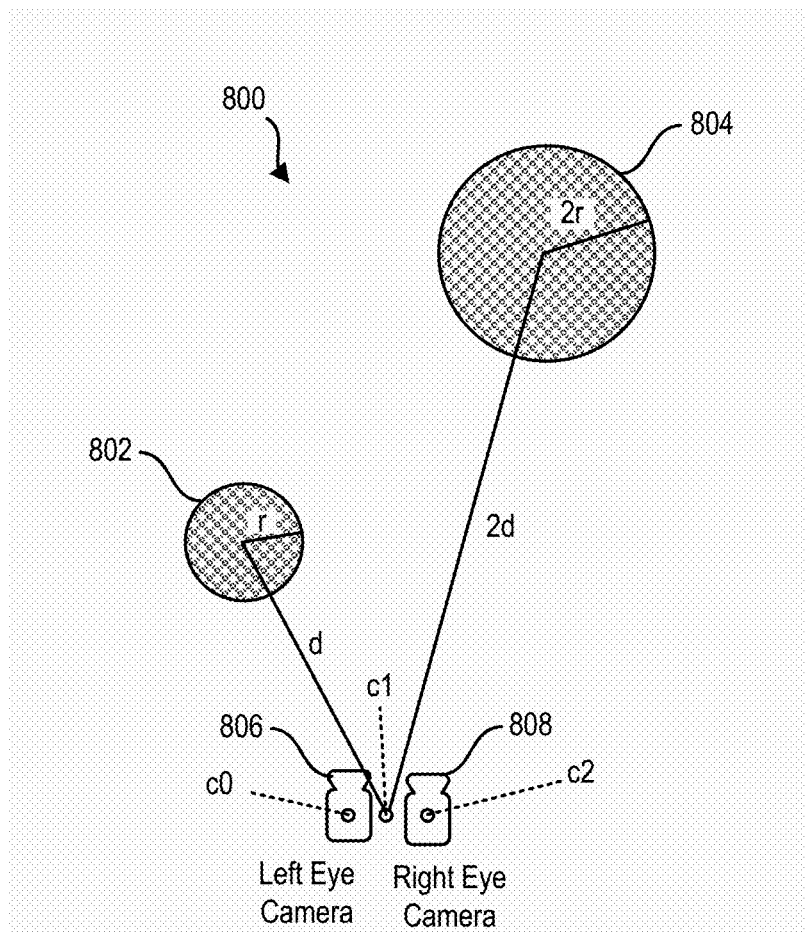
FIG. 8A is a schematic diagram illustrating objects displayed to a user to measure user's depth perception.
Figure 8B:
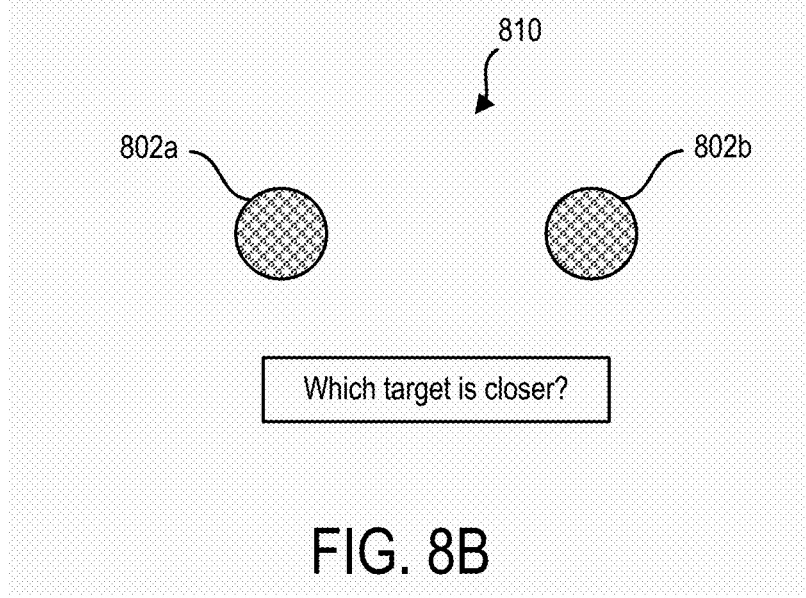
FIG. 8B is a schematic diagram illustrating the objects of FIG. 8A as visible to the user.

To measure a depth perception, two objects can be shown to both user's eyes and the user's ability to perceive a distance between the objects is assessed, as shown in FIGS. 8A and 8B. As shown schematically in FIG. 8A illustrating a representation 800 of a scene to be presented to the user showing a realistic relationship between first and second objects 802, 804, a scale, or radius (r), and a distance (d) between each of the objects and a mid-point (c1) between cameras of a VR display is selected such that an apparent size of the first and second objects 802, 804 is the same. The cameras include a left eye camera 806 having a position at a point (c0) and a right eye camera 808 having a position at a point (c2), the cameras 806, 808 shown as disposed to the left and right of the mid-point (c1), respectively. If higher image resolution is desired to test stereoacuities, a lens system such as the system 700 (FIG. 7) can be used.

In this example, because the second object 804 is twice as far away from the mid-point (c1) as the first object 802, the radius of the second object 804 is twice the radius of the first object 802. Thus, as shown in FIG. 8A, the first object 802 having a radius r is at a distance d from the point c1 and the second object 804 having a radius 2r is at a distance 2d from the point (c1).

The first and second objects are displayed such that there are no monocular cues that would be helpful to the user to determine the distance between the objects. FIG. 8B illustrates a user's view 810 where the first and second objects 802, 804 of FIG. 8A are shown as first and second objects 802a, 804a. As shown in FIG. 8B, depending on a severity of the user's depth perception disorder, the first and second objects can appear to be of the same size or approximately of the same size to the user. A user having the disorder can also lack a perception of the distance between the user's eyes and the objects.

As also shown in FIG. 8B, a prompt 812 can be displayed to the user requesting user's input regarding which of the first and second objects 802a, 804a the user perceives to be closer. Additionally or alternatively, the prompt can include an inquiry which of the objects the user perceives to be smaller. It should be appreciated that the prompt 812 can be presented in any suitable format, including a format that is different from textual, such as a voice prompt or any other format. The user input can be received in a number of different ways. For example, it can be acquired via an input device (e.g., one of the devices 214 in FIG. 2), as a voice input, or in any other manner.

After a user input indicating a user's selection of one of the displayed objects 802, 804 in response to the prompt 812, the test can be repeated a number of times. At each repetition of the test, two objects can be placed at different distances from the user's eyes. A size of the objects can also vary from one iteration to another. For example, a position of each object on the scene, a distance between the objects, a scale and a distance to each object from the cameras can be randomly selected, to avoid biasing the results toward one of the eyes. Different properties of the objects, such as a contrast, color, texture, shape, movement, etc., can also be selected for each repetition of the test. These values can be selected in any manner, for example, randomly, to avoid biasing the results toward one of the eyes. The user's view 810 can include a moving background behind the objects, and the test can be conducted both with the background and without the background. After it is determined that sufficient amount of data is acquired, which can indicate that a reliable assessment of the user's depth perception can be made, the test can be completed.

The user's view 810 can include a moving background behind the objects, and the test can be conducted both with the background and without the background.

Determining the Dominant Eye

Figure 9:
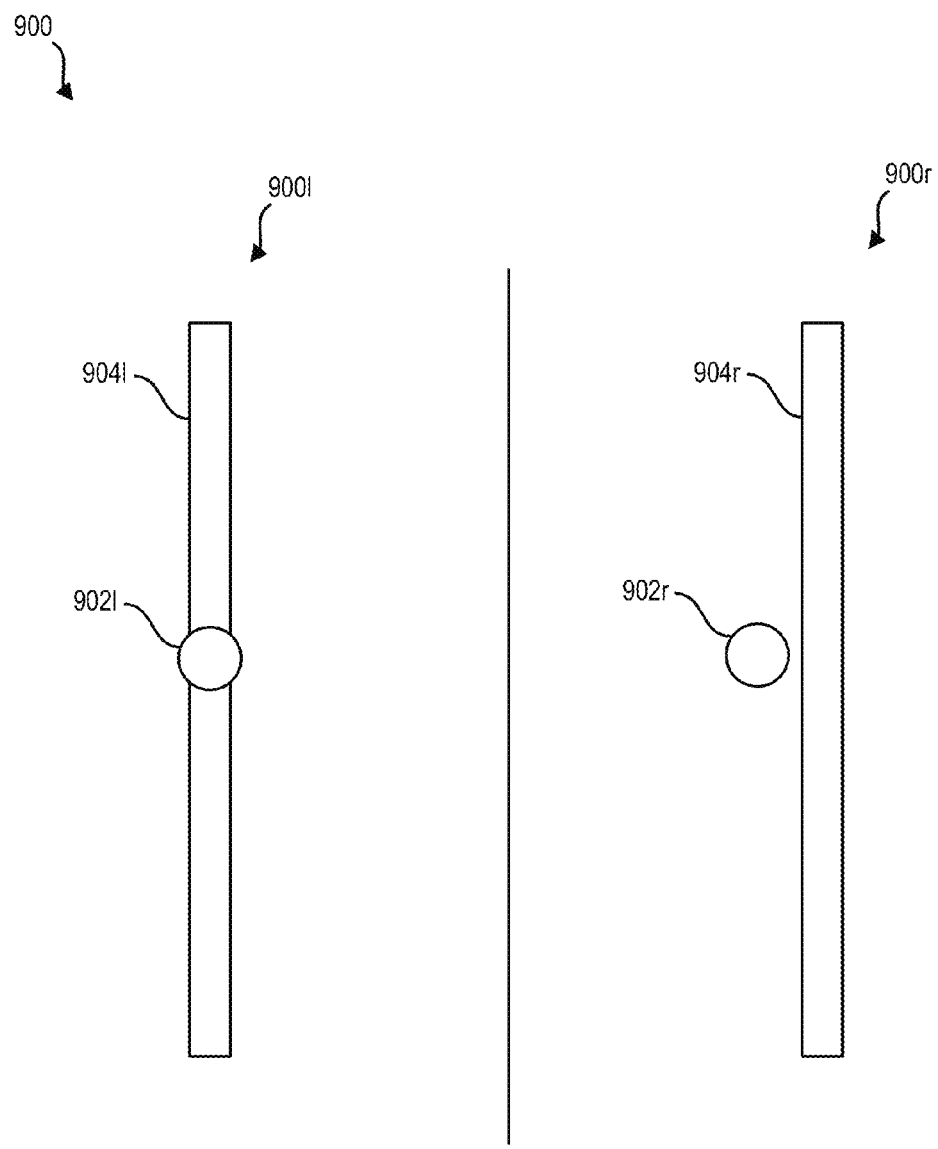
FIG. 9 is a schematic diagram illustrating images presented to the left and right eyes of the user during an activity to determine a dominant eye.

FIG. 9 is a diagram 900 showing an image 900l presented to the user's left eye and an image 900r presented to the user's right eye to determine the dominant eye of the user. A small object 902 closer to the user and a larger object 904 at a large distance from the user are shown. The small object is schematically shown as an object 902l on the image 900l and an object 902r on the image 900l, and the large object is schematically shown as an object 904l on the image 900l and an object 904r on the image 900r. The user is instructed to line up the small object 902 with the distant object 904. User input can be received based on tracking user's eye movement, or in other manner. If the eye tracking technology is used, rays can be transmitted from each of the left eye and right eye cameras of a VR display. If the ray transmitted from one of the cameras hits the small, closer object 902, the eye that the camera is dedicated to is determined to be dominant. Thus, in the example of FIG. 9, the left eye of the user is determined to be dominant, because the small, closer object 902 is aligned with the large, distant object 904 in the left eye only.

Determining Suppression of an Eye

Figure 10:
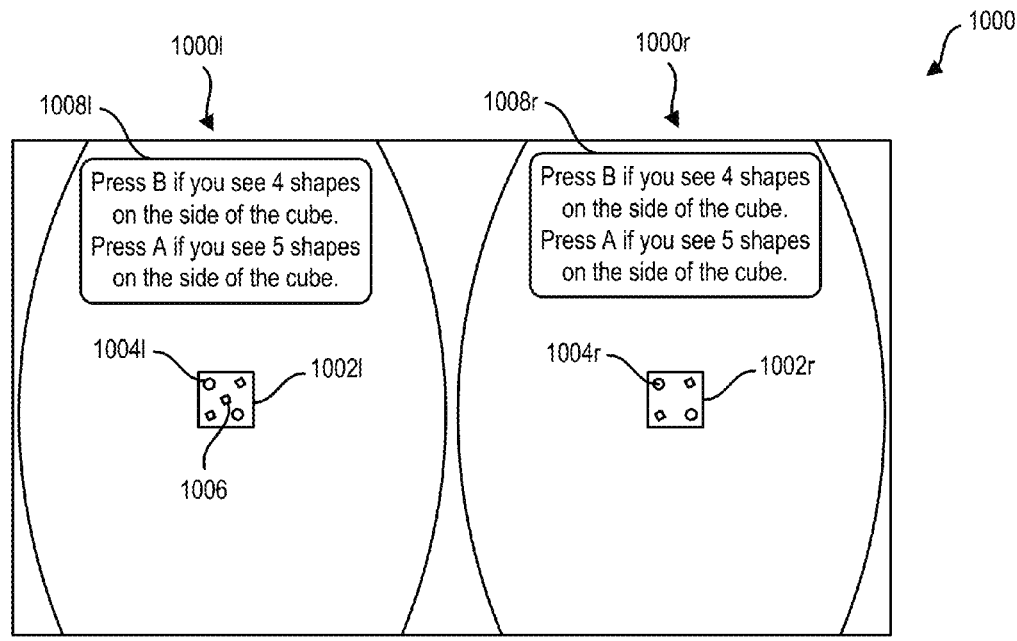
FIG. 10 is a schematic diagram illustrating images presented to the left and right eyes of the user during an activity to determine suppression of a weak eye.

FIG. 10 is a diagram 1000 showing an image 1000l presented to the user's left eye and an image 1000r presented to the user's right eye to determine suppression of a weak eye. Squares 1002l and 1002r are shown to both left and right eyes. Each of the squares 1002*l*, 1002*r* has four symbols of different shapes (in this example, two circles and two squares). However, an additional symbol can be shown to the amblyopic eye which is, in this example, is the left eye. Thus, as shown in FIG. 10, the "left" square 1002*l* displayed to the left eye includes an additional symbol 1006 in the middle thereof. In the test for determining suppression of the weak eye, any number and types of shapes can be used having different properties (e.g., color, texture, size, etc.), and the squares 1002*l* and 1002*r* having the symbols are shown in FIG. 10 by way of example only.

As shown in FIG. 10, the user can be prompted (1008*l* and 1008*r*) to indicate whether he or she can see four shapes ("Press B if you see 4 shapes on the side of the cube" or five shapes "Press A if you see 5 shapes on the side of the cube"). It should be appreciated that the above prompt is shown by way of example only, as any other type of prompt can be presented to the user in any format. If user input is received indicating that the use can see all five symbols, the luminance of the displayed symbols with respect to the background can be decreased in the amblyopic (left, in this example) eye, while the luminance of the symbols with respect to the background displayed to the other (right, in this example) eye remains unchanged. If after the luminance is decreased the user cannot see all of the five symbols, the luminance is increased. A suitable approach can be used to determine a threshold luminance at which the user can still (but with difficulties) see the center symbol 1006. For example, a staircase algorithm can be used to determine the threshold luminance.

Figure 11:
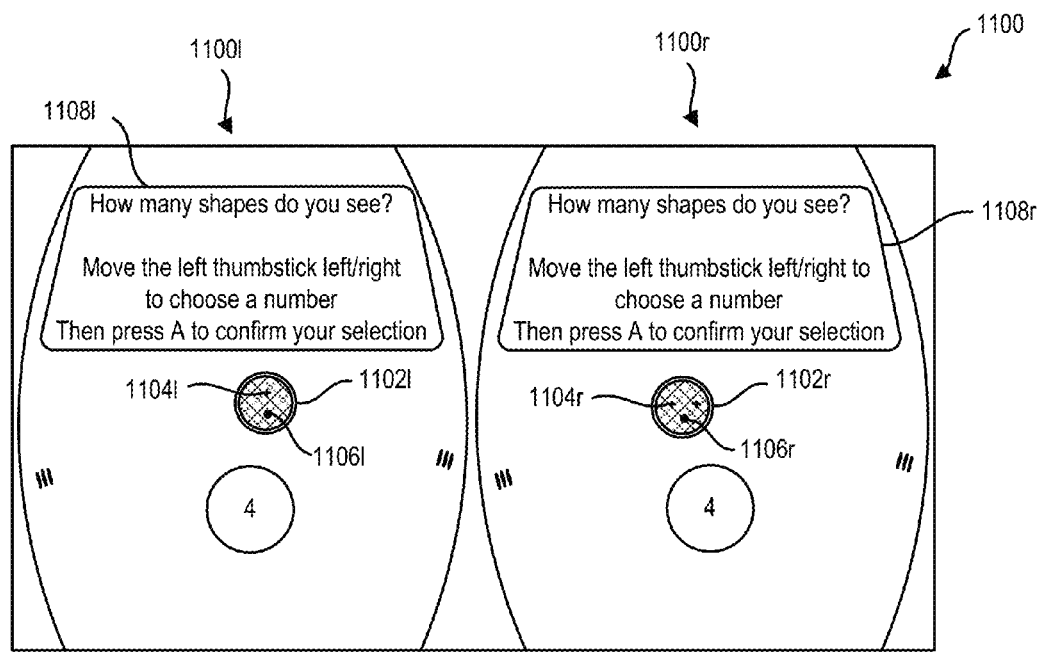
FIG. 11 is another schematic diagram illustrating images presented to the left and right eyes of the user during an activity to determine suppression of a weak eye.

FIG. 11 is another diagram 1100 showing an image 1100*l* presented to the user's left eye and an image 1100*r* presented to the user's right eye to determine suppression of a weak eye. Black circles 1102*l* and 1102*r* are shown to both left and right eye. As shown in FIG. 11, the circle 1102*l* shown to the left eye includes two symbols (e.g., red symbols) and the circle 1102*r* shown to the right eye includes three symbols (e.g., green symbols). The symbol in the form of a circle on the bottom of the circles 1102*l* and 1102*r* is shown as a circle 1106*l* and a circle 1106*r* such that the circles 1106*l*, 1106*r* are present in the same location within a scene in both eyes.

As shown in FIG. 11, the user is presented a prompt (1108*r* and 1108*r*) asking the user to identify how many shapes (or symbols) the user can see. The user is also instructed to provide input in accordance with the number of visible shapes. If the user input indicates that the user can see two symbols, the right eye is determined to be heavily suppressed. However, if the user input indicates that the user can see three symbols, the left eye is determined to be heavily suppressed. If the user input indicates that the user is able to see four symbols, this indicates that the user's eyes properly fuse the different images presented to the left and right eyes.

The user can also be asked to specify what is the color of the bottom circle symbol within the larger circle 1102, shown as the circle 1106*l* and the circle 1106*r*. If the user input indicates that the user perceives the bottom circle as green, it is determined that the left eye is suppressed. Alternatively, if the user input indicates that the user perceives the bottom circle as red, it is determined that the right eye is suppressed. If the user input indicates a mixture of red and green or white, it can be determined that proper fusion is obtained. The test can be repeated for different angular sizes of the circle 1102 (shown as 1102*l* and 1102*r*) and with various symbols of different shapes and colors, to test suppression of an eye at different spatial frequencies.

Figure 12:
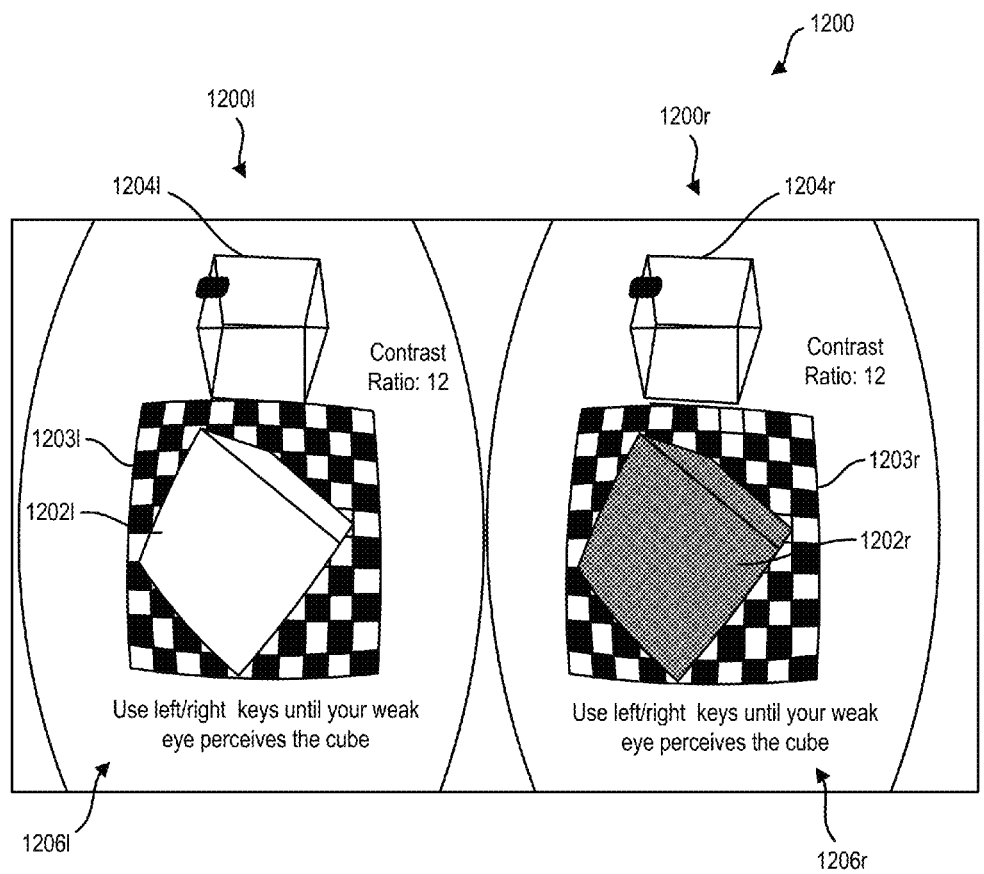
FIG. 12 is another schematic diagram illustrating images presented to the left and right eyes of the user during an activity to determine suppression of a weak eye.

FIG. 12 is another diagram 1200 showing an image 1200*l* presented to the user's left eye and an image 1200*r* presented to the user's right eye to determine suppression of a weak eye. An object, such as a cube in this example, is shown to both eyes. Thus, the object 1202 is shown as a cube 1202*l* and a cube 1202*r* to the left and right eyes, respectively. The cubes 1202*l*, 1202*r* can have different respective backgrounds 1203*l*, 1203*r*, as shown in FIG. 12. The object 1202 can be rotated or otherwise manipulated based on user input and respective representations of the movement of the object 1202 are shown as representations 1204*r* and 1204*l* in FIG. 12.

Values of various parameters of the object 1202 can be adjusted until the user perceives the object 1202 with both eyes. For example, a contrast, brightness, color, saturation, position, orientation, pattern of motion, direction of motion, speed of rotation of the object 1202, or other parameters can be adjusted. The values of these and/or other parameters can be adjusted automatically (e.g., by a platform implementing the test of FIG. 12) or based on user input received either from the user undergoing the test or from an operator (e.g., a clinician) of a device controlling the execution of the test. For example, FIG. 12 shows that the user can be presented with a prompt (1206*r* and 1206*l*) instructing the user to provide input until the object 1202 is visible to both eyes ("Use left/right keys until your weak eye perceives the cube"). Values of one or more parameters can be displayed to the user (e.g., "Contrast Ratio: 1"). It should be appreciated that any other parameter values can be displayed or the display of the values of the parameters can be omitted. The values of the parameters at which the user can perceive the object 1202 with both eyes can be used to measure the suppression of a weak eye.

The test of FIG. 12 can be repeated multiple times, with a number of different objects shown separately to each eye, to ultimately determine a threshold value indicating a measure of the magnitude of the user's interocular suppression. The users can be prompted to identify a direction of motion or rotation of the objects in their weak eye. Different number of objects can be presented at each repetition of the test, which can also be selected based on user input.

In some aspects, to determine suppression of a weak eye in a manner similar to the one shown in connection with FIG. 12, a plurality of objects can be shown separately to both eyes and the user is instructed to "interact" with the objects. Based on the user's interaction with the objects, a contrast, brightness, color, saturation, number of objects, direction of movement of the objects, speed of movement of the objects, or rotation of the objects can be adjusted in real-time, as the user is undergoing the test. After multiple adjustments at each iteration, a threshold value can be determined that indicates a measure of the magnitude of the user's interocular suppression.

Measuring Alignment of the Eyes

Figures 13A, 13B:
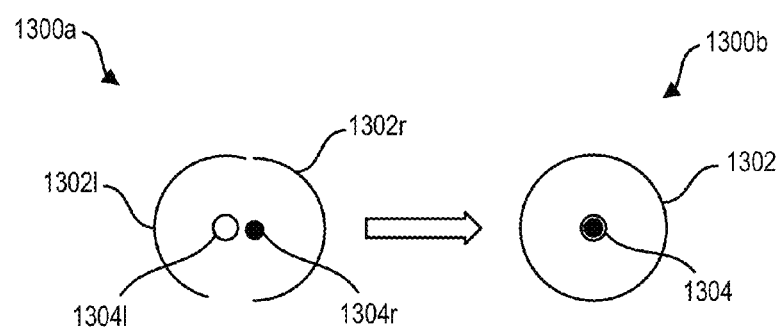
FIG. 13A is a schematic diagram illustrating an image displayed to the user during an activity intended to measure alignment of the user's eye, showing the image as initially displayed to the user.
FIG. 13B is a schematic diagram illustrating an image displayed to the user during an activity to measure alignment of the user's eye, showing the image after displayed objects are "aligned" by the user.

To measure alignment of the user's eyes, two or more objects can be displayed to the user using respective different representations for the left and right eyes. FIGS. 13A and 13B illustrate a process of assessing ability of user's eyes to align with respect to one another objects displayed on a VR display. In this example, a half of a crosshair shape can be shown to each eye at 0.1 second to 1 second intervals in an alternate manner. FIG. 13A is a diagram 1300*a* showing arcuate shapes or halves 1302*l*, 1302*r* displayed to the left and right eyes, respectively, before alignment. The shapes 1302*l*, 1302*r* form halves of the crosshair shape. The shapes 1302*l*, 1302*r* can have different thicknesses and, in some cases, they can have different colors. FIG. 13A also shows circular shapes 1304*l*, 1304*r* disposed mid-way between opposite ends of each of the arcuate shapes 1302*l*, 1304*r* and displayed to the left and right eyes, respectively, before alignment.

The user can be instructed to look forward and to provide input such that each of the halves 1302*l*, 1304*r* is moved until their circular shapes 1304*l*, 1304*r* line up into one circle 1304, as shown in FIG. 13B. The user can further be instructed to provide input to rotate each of the halves 1302*l*, 1302*r* until they are aligned and form a circle 1302, as also shown in FIG. 13B. The user can also be to rescale one of the halves 1302*l*, 1304*r* until they align into the circle 1302 drawn using a uniform thickness of the outer line. Such operations can be used to determine an angle of deviation, scale deviation, and rotational deviation of the user's eyes.

In some aspects, measure alignment of the user's eyes, a scene including one or more moving objects can be presented to both eyes and then to each eye individually. The user can be instructed to "follow" the moving objects with his or her gaze. Eye tracking technology, such as sensors incorporated into a head-mountable VR device being used, can be used to acquire eye movement data to determine an angle of deviation between the user's eyes based on user's looking at the objects located in the same virtual spot.

As another variation of measuring alignment of the user's eyes, if it is determined that the user is not able to use both of his or her eyes at the same time (e.g., due to suppression or for some other reason), a target object can be displayed and the user is prompted to align the object with eye individually.

Determining Interpupillary Distance

In some aspects, to determine interpupillary distance, one or more moving objects can be displayed to both eyes of the user, with the objects being locked to their field of view. The objects can then be displayed to each eye individually, and the user is instructed to follow the objects as they move. The objects can be displayed to the user for a certain amount of time. Eye tracking technology can be used to determine when the user is no longer able to track the objects, and the interpupillary distance can then be determined.

Figure 14A:
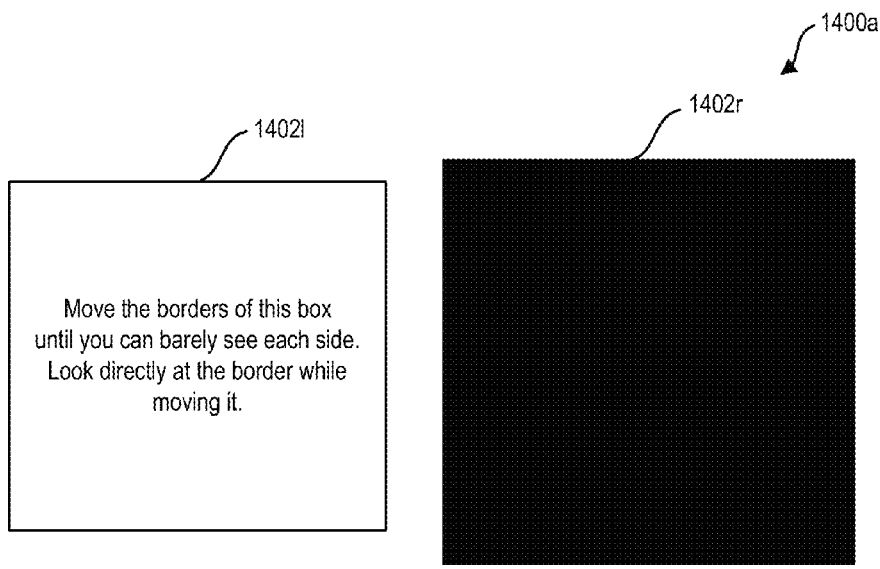
FIGS. 14A and 14B are schematic diagrams illustrating exemplary scenes displayed to the user during an activity to measure user's interpupillary distance.
Figure 14B:
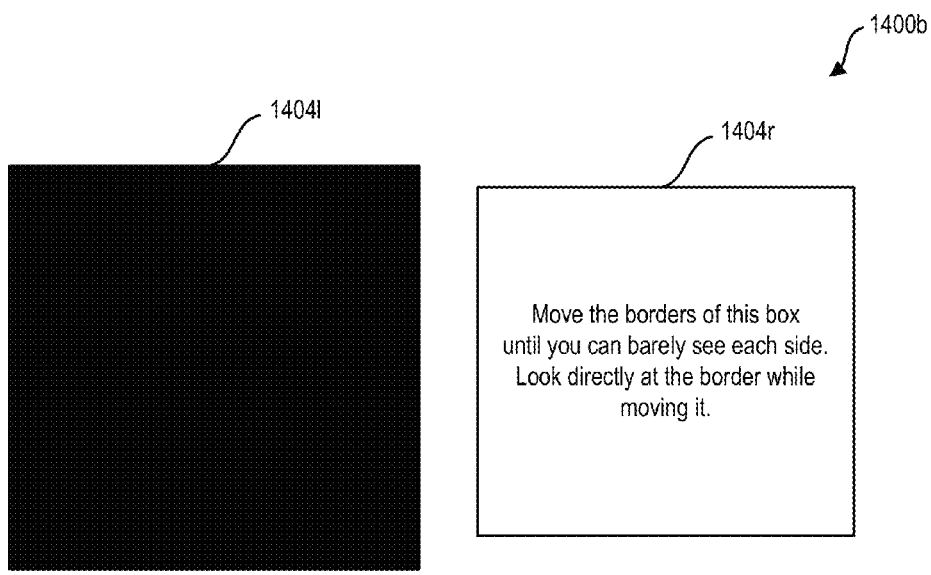

FIGS. 14A and 14B illustrate exemplary scenes 1400*a*, 1400*b* presented to the user to determine user's interpupillary distance. As shown in FIG. 14A, a square 1402*l* can be presented to one eye (left, in this example) while the other eye (right, in this example) is blocked which is schematically shown as a black box 1402*r* indicating that no image is delivered to the right eye. As shown with a text within the square 1402*l*, the user is then instructed to look at the square 1402*l* and "move" its borders towards the edge of the field of view until the user can just barely see the edges of the field of view while looking directly at them. The test can then be changed such that a square 1404*r* is presented to the right eye whereas the left eye is blocked (1404*l*), as shown in FIG. 14B. The user can receive the same instruction with respect to the square 1404*r*. By knowing the dimensions and position of the head-mountable screen with respect to the viewer's face combined with the values of the borders of the box on the screen, an interpupillary distance can be calculated. An interpupillary distance can be determined and refined based on one or more iterations of the test including displaying to the user scenes similar to those shown in FIGS. 14A and 14B.

Breaking Suppression

Figure 15:
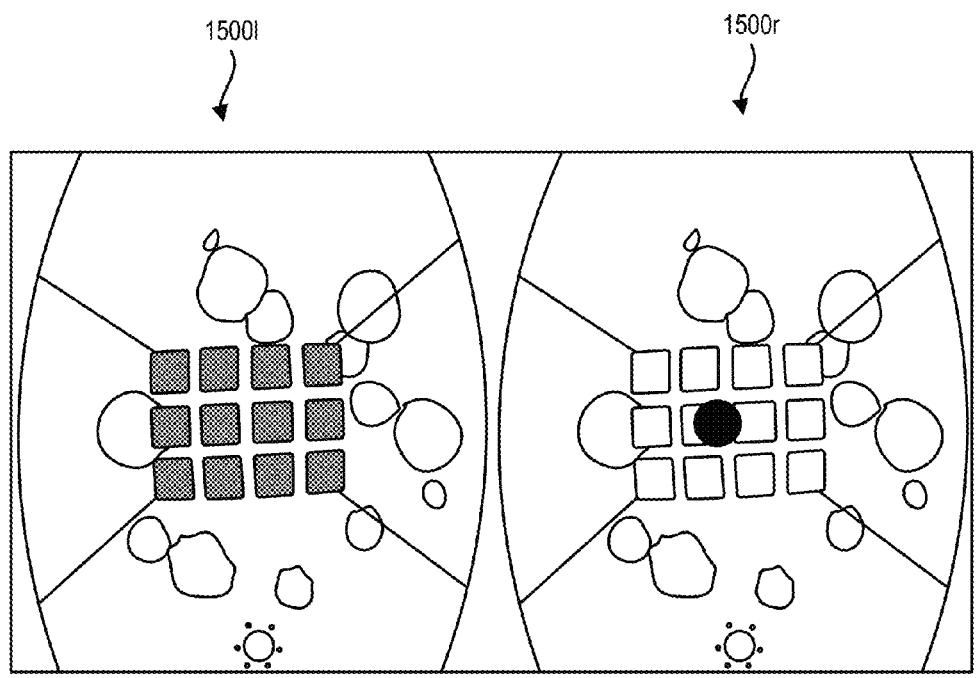
FIG. 15 is a schematic diagram illustrating images presented to the left and right eyes of the user during an activity to break suppression of a weak eye.

To break, or alleviate, suppression of a weak, amblyopic eye, the same objects can be displayed on images presented to both eyes. The objects can have different colors, contrast, saturation, or other properties selected such that enough information is provided for the user's brain to integrate the images delivered to each eye. Strong outlines and shapes with high contrast against a background can be used so as to help to reduce the suppression of the weaker eye. For example, FIG. 15 illustrates an image 1500*l* that can be displayed to the left eye and an image 1500*r* that can be displayed to the right eye during an activity intended to train the user to break suppression of the weak eye.

In some aspects, to break suppression of the weak eye, the same objects can be rendered to both eyes, and a color, contrast, brightness, saturation, and/or other properties of the objects can be adjusted individually on each eye. The adjustment process can be repeated multiple times (e.g., more than 10 times per second) between the two eyes.

In some aspects, to break suppression of a weak eye, the same object can be rendered to one eye at a time. The images of the objects alternate between the eyes a number of times per second (e.g., more than 10 times per second) to create a strobe-like effect.

In some aspects, to break suppression of a weak eye, a field of view can be measured. If it is determined that one or more areas of the field of view are suppressed on each eye (as in alternating esotropia), a scene can be rendered to each eye only in the areas where the scene is suppressed, forcing that eye to use the suppressed areas.

In some aspects, to break suppression of a weak eye, lights can be flashed inside a head-mountable VR display 7-10 times a second, with the flashes alternating to each eye.

Figure 16:
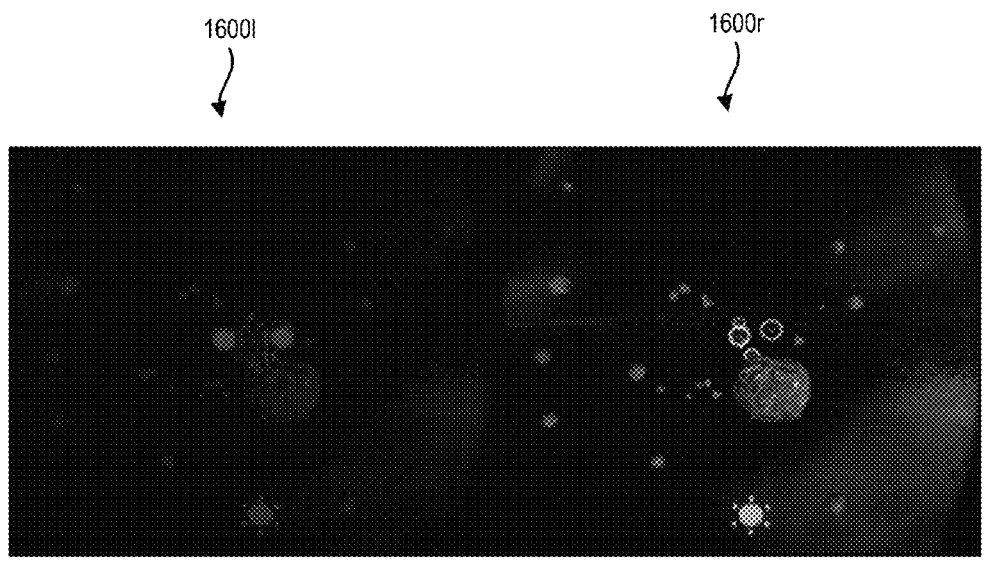
FIG. 16 is another schematic diagram illustrating images presented to the left and right eyes of the user during an activity to break suppression of a weak eye.

Any of the above approaches to breaking suppression of a weak eye can be used in conjunction with either totally or partially occluding the stronger eye. By decreasing the image signal delivered to the stronger eye, a threshold at which the user begins to use the suppressed, amblyopic eye, can be determined. For example, FIG. 16 illustrates an image 1600*l* that can be displayed to the left eye and an image 1600*r* that can be displayed to the right eye during an activity intended to train the user to break suppression of a weak eye. In FIG. 16, the image 1600*l* shown to the user's strong (left) eye is a lower signal image compared to the image 1600*r* which is shown to the user's weak (right) eye in order to break or reduce suppression of the amblyopic eye.

Figure 17:
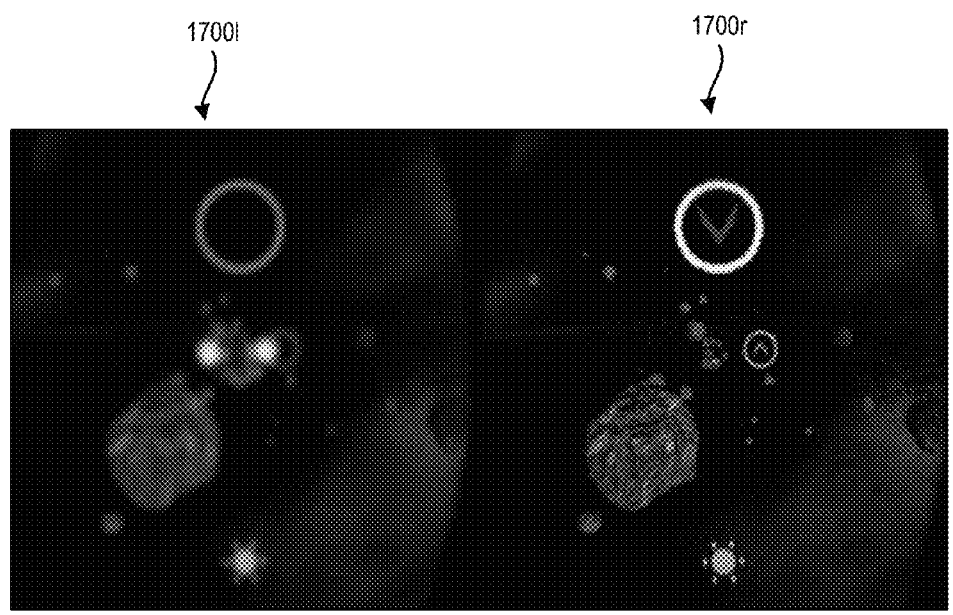
FIG. 17 is another schematic diagram illustrating images presented to the left and right eyes of the user during an activity to break suppression of a weak eye.

Any of the above approaches to breaking suppression of a weak eye also can be used in conjunction with either totally or partially blurring the stronger eye. By decreasing the image signal delivered to the stronger eye, a threshold at which the user begins to use the suppressed, amblyopic eye, can be determined. For example, FIG. 17 illustrates an image 1700*l* that can be displayed to the left eye and an image 1700*r* that can be displayed to the right eye during an activity intended to train the user to break suppression of a weak eye. In FIG. 17, the image 1700*l* shown to the user's strong (left) eye is blurred while the image 1700*r* which is shown to the user's weak (right) eye is not blurred in order to break suppression.

Measuring Balancing Tasks

People with binocular vision problems can be trained faster by being forced to actively balance while doing the vision exercises. Thus, a user performing a visual activity can be prompted to balance on one foot or perform other balancing task while a head tracking technology can be used to track duration of a period of time during which the user is able to balance during the activity. Data related to user's ability to perform the balancing task can be acquired (e.g., using along appropriate sensors) along with the results of the current visual activity. It should be appreciated that various types of balancing tasks can be used in association with any suitable visual activity.

Measuring and Mitigating Head Tilting

People who favor one eye over the other often tilt their head to help compensate for the weaker eye. Thus, a head tracking technology can be used to acquire data relating to a position and/or rotation of the user's head during performance of a visual activity. The data can then be used to detect an amount of tilt of the user's head, and this information can be used to encourage the user to refrain from tilting his or her head. For example, voice, textual, graphical, or other prompts can be used to instruct the user to keep his or her head leveled. The user can also be penalized (e.g., as part of a visual activity embodied as a game) for tilting his or her head.

Strengthening a Weak Eye and Training the Brain to Use the Weak Eye

Figure 18:
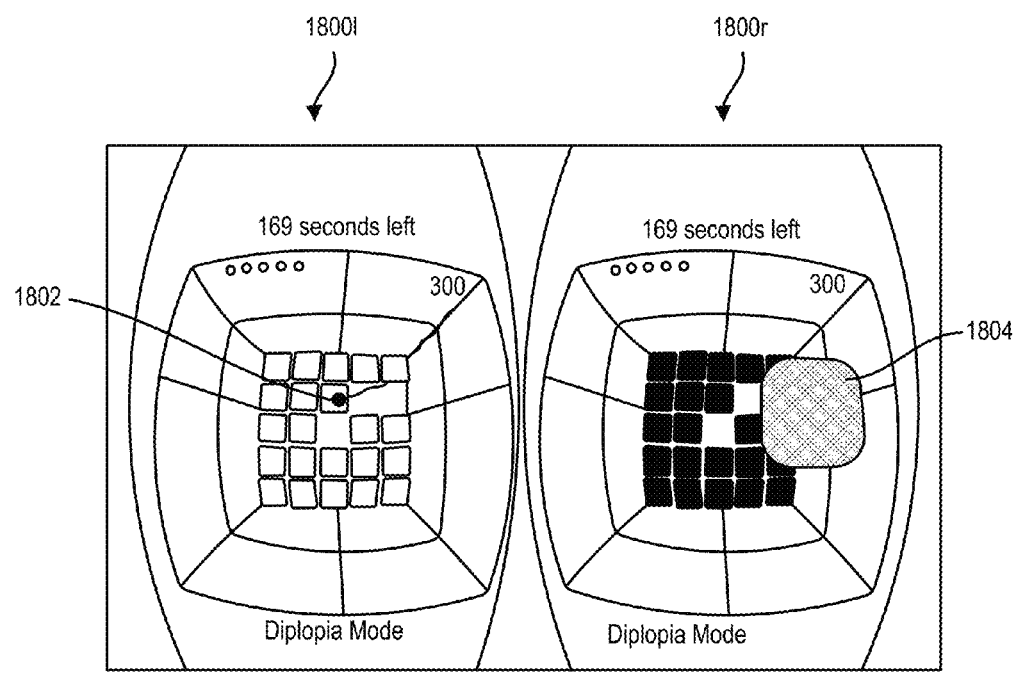
FIG. 18 is a schematic diagram illustrating images presented to the left and right eyes of the user during an activity to strengthen a weak eye.

An activity intended to strengthen a weak eye can be in the form of a 3D game where users can actively follow tracked objects with their weak eye. For example, at least one object can be displayed to the user with different contrast, brightness, color, saturation, or other properties. An object can be displayed to the stronger eye of the user as a controllable object, meaning that user input can be received with respect to the object. One or more objects the user has to intersect or avoid (tracked objects) can be displayed to the weaker eye. For example, FIG. 18 illustrates an image 1800*l* that can be displayed to the left eye and an image 1800*r* that can be displayed to the right eye during an activity intended to strengthen a weak eye.

The user can be instructed to follow a tracked object 1802 with the left eye which is, in this example, the left eye of the user. The user can then be instructed to provide input to move a controllable object 1804 to intersect or avoid the tracked object 1802. This requires the user's brain to use information coming from both eyes to win the game. Additionally, the two images have to line up spatially for the user to be able to intersect or avoid the tracked object with the controllable object. It should be appreciated that more than one tracked or controllable objects can be displayed of any suitable type and size.

By playing a game as described above, the user is forced to actively use the weaker eye muscle, thus strengthening that eye. Suppression of the weak eye as well as angles of deviation can be periodically measured to adjust gameplay and contrast, brightness, color, or saturation of game elements as the suppression of the user's weak eye changes.

Jump Duction

An activity can include displaying a small target object to the user viewing the object with spatial frequency just above the user's acuity, in order to measure the ranges over which the user's eyes can successfully fuse an image being shown with binocular disparity. The binocular disparity of the target object can be increased horizontally until user input received from the user indicates that the user perceives the target object as blurry. The activity can be repeated until the acquired user input indicates that the user seeing a double of the displayed object, which is the outer limit of the user's fusional range. The disparity can then be reduced until the user indicates that the target object is blurry, then until the user indicates that the target object is perceived as a single object again. This is the inner limit of the user's fusional range. The amount of disparity at each point is a measure of the user's blur, break, and recovery. These three points provide a measurement over the fusional ranges of the viewer.

Cover Test

An activity can include virtually "covering" the dominant eye (e.g., by "greying" it out or otherwise preventing its use). A distant target object can be displayed to the user while the "covered" dominant eye is "uncovered." Using eye tracking technology, it is then measured which direction the dominant eye moves once it is "uncovered." If the eye moves inward, it can be determined that the user has exophoria which is a tendency of the eyes to deviate outward. However if the eye moves outward, it can be determined that the user has exophoria characterized by inward deviation of the eyes. The activity can be repeated with a target object displayed closer to the user (a near target).

Measuring Fusional Ranges

An image of an object from a plurality of different target objects is shown to both eyes of a user such that the same representation of the object is delivered to both eyes. The deviation between the representations of the object can then be increased (e.g., moved closer in the virtual space) until a user input is received indicating that the object is perceived as blurry. The deviation is then increased further until a user input is received indicating that the image of the object is perceived as double. The deviation between the representations of the object delivered to the left and right eyes can then be decreased until a user input is received indicating that the image of the object is perceived as blurry, and then until a user input is received indicating that a single image is perceived. These measurements together can be taken as a measure of fusional range.

Visual Acuity

Figure 19:
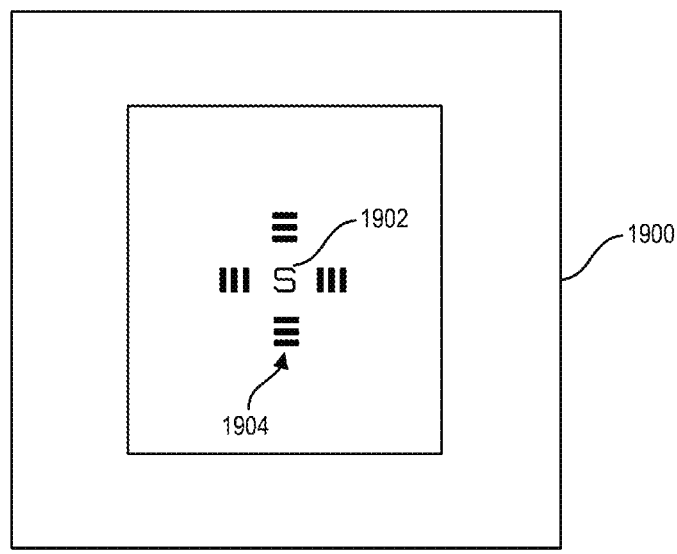
FIG. 19 is a schematic diagram illustrating an image presented to at least one of the left and right eyes of the user to perform an acuity test.

A number of various acuity tests can be performed in accordance with various implementations of the current subject matter. Objects such as, for example, letters, numbers, or symbols with crowding bars, can be displayed during the acuity tests. The user can be instructed to indicate objects and properties of the objects that the user can see. FIG. 19 is an exemplary image 1900 that can be displayed to a user to perform an acuity test. As shown in FIG. 19, the image 1900 includes a central symbol 1902 in the form of a letter "S" and four sets of three crowing bars 1904 disposed on the top, bottom, and to the left and right from the central symbol 1902.

Nearsighted Acuity

To measure nearsighted acuity, objects such as, for example, letters, numbers, or symbols with crowding bars (e.g., as shown in FIG. 19), can be presented to the user. A transparent or semi-transparent display (e.g., a computer screen, projector or other display) associated with a computing device can be used in addition to a VR display of a VR device worn by the user. The user can be instructed to stand a specified distance from the display. One or more objects such as letters, numbers, arrows, words, or any other symbols can be displayed on that display, and the user can be instructed to indicate in a suitable manner which objects and properties of the objects the user can perceive. The user input can be acquired via, for example, a suitable user interface, such as a user interface displayed on the VR display, using head tracking technology, and/or via one or more input device.

A symbol of a certain (known) size can be displayed on the transparent or semi-transparent display such that a size and shape of the symbol allows determining a distance and position with respect to the display. The size, color, position, brightness, or contrast can be adjusted between each user input, and the user input is used to determine whether the user was correct. After a number of adjustment iterations, a threshold value can be determined which can then be stored as a measurement of the magnitude of the user's visual acuity.

As another exemplary way to measure user's visual acuity, an activity can include displaying letters, numbers, arrows, words, or other symbols on the VR display. User input is collected with respect to what the user can see. At each iteration, an apparent size of one or more of the objects can be made smaller until errors in user's perception of the displayed objects reach a certain threshold. The activity can be conducted on the left eye, then on the right eye, and then on both eyes, to determined respective acuity values.

Farsighted Acuity

To measure farsighted acuity, appropriate optics set can be used. To measure farsighted acuity, similarly to measuring the nearsighted acuity, objects such as, for example, letters, numbers, or symbols with crowding bars (e.g., as shown in FIG. 19), can be presented to the user. An activity can include displaying letters, numbers, arrows, words, or other symbols on the VR display. User input is collected with respect to what the user can see. At each iteration, an apparent size of one or more of the objects can be made smaller until errors in user's perception of the displayed objects reach a certain threshold. The activity can be conducted on the left eye, then on the right eye, and then on both eyes, to determined respective acuity values.

In some aspects, to measure farsighted acuity, a transparent or semi-transparent display can be used so as to have the user stand a distance from their computer. Objects such as, for example, letters, numbers, arrows, or words, can be displayed on a separate display, which can be, for example, a smartphone, computer, TV, or tablet. Head and/or eye tracking sensors of the VR device worn by the user, and a user interface of the VR display can be used to acquire user input with respect to user's ability to perceive the displayed objects.

A symbol of a certain (known) size can be displayed on a separate display, which can be, for example, a smartphone, computer, TV, or tablet, such that a size and shape of the symbol allows determining a distance and position with respect to the computer screen/projector. The size, color, position, brightness, or contrast can be adjusted between each user input, and the user input is used to determine whether the user was correct. After a number of adjustment iterations, a threshold value can be determined which can then be stored as a measurement of the magnitude of the user's visual acuity.

Improving Visual Acuity

Figure 20:
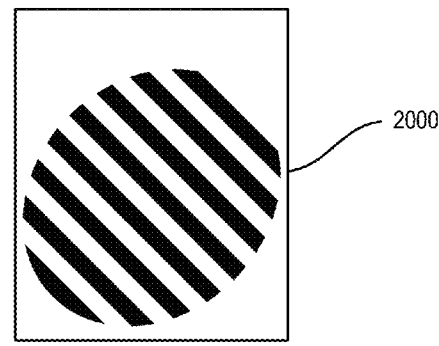
FIG. 20 is a schematic diagram illustrating a Gabor patch.

An activity intended to improve user's visual acuity can be in the form of a game that involves displaying a plurality of objects on a scene. At least one of the objects can have a Gabor patch, such as a patch 2000 shown in FIG. 20, rendered over them. The user can play a game such that the user can interact with each object in the scene using an input device (e.g., mouse, keyboard, gamepad controller, or a head-mounted VR display). The user is "rewarded" with suitable visual and auditory feedback for interacting with the objects which have Gabor patches rendered on them.

An activity intended to improve user's visual acuity can also involve displaying a shape (such as a letter) with a low contrast at a fixed size to only the amblyopic eye. The same shape can then be shown to the other eye at extremely low contrast that can be then increased until user input is acquired indicating that the user can identify the shape and its properties. If it is determined that the user is able to identify the shape with just his or her amblyopic eye, a size, contrast, and/or other properties of the shape can be modified and the activity is repeated with the modified shape displayed to the user.

Tracking

Measuring Perception of Movement

An activity intended to measure user's perception of movement can involve displaying to the user a scene having an object such that user input can be acquired in response to user's noticing the object (tracked object). The rendered scene images are sent to one or both eyes during the activity. Eye tracking sensors can be used to record where one or both of the user's eyes are looking during the activity.

An activity intended to measure user's perception of movement can also involve displaying to the user a scene including a text which the user is instructed to read. The text can be shown for a short time, at various speeds (e.g., for a time period in a range from 0.1 seconds to 2 seconds) to the left, right, or both eyes. The user is instructed to type the text visible to the user and the accuracy of the text being reproduced by the user is measured. The user can be instructed to type the characters in sequential or reverse order. Text strings can be added to the scene one at a time at different positions, velocities, sizes, brightness, contrast, color, and movement patterns.

An activity intended to measure user's perception of movement can involve displaying to the user a scene having an object such that user input can be acquired in response to user's noticing the object (tracked object). The rendered scene images are sent to one or both eyes during the activity. The user can be instructed to keep his or her gaze at a fixed point in the scene throughout the activity. Tracked objects can be added one at a time to the scene at different positions, velocities, sizes, brightness, contrast, color, and movement patterns. By logging information on tracked objects the user is able to perceive, a 3D map of user's perception of motion can be generated. The activity can be repeated for a number of times sufficient to generate a map for the left eye, right eye, and both eyes.

Visual Field

Measuring Parameters Across the Visual Field

Figure 21:
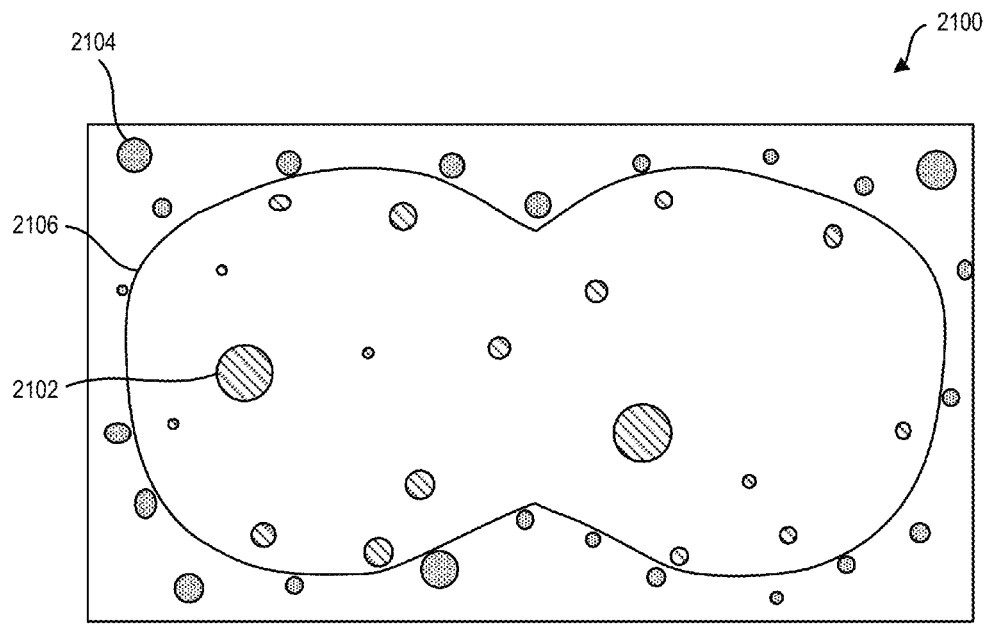
FIG. 21 is a schematic diagram illustrating a 3D map generated as a result of an activity measuring user's field of view.

An activity intended to measure user's visual field in 3D can involve displaying a scene having an object such that user input can be acquired in response to user's noticing the object or certain properties of that object (tracked object). The rendered scene images are sent to one or both eyes during the activity. The user can be instructed to keep his or her gaze at a fixed point in the scene throughout the activity. Tracked objects can be added one at a time to the scene at different positions, velocities, sizes, brightness, contrast, color, stereo disparities using Randot tests, and movement patterns. By logging information on tracked objects the user is able to perceive, a 3D map of the user's field of view can be generated. The activity can be repeated for a number of times sufficient to generate a map of the specified parameter for the left eye, right eye, and both eyes. FIG. 21 is a diagram illustrating an exemplary map 2100 of the user's field of view including tracked objects 2102 that are successfully perceived by the user, tracked objects 2104 that are not perceived by the user, and a measured field of view 2106.

An activity intended to measure the user's field of view can also involve displaying objects in a 3D scene such that the objects are offset from a fixation point of the eye. As before, eye tracking sensors can then be used to determine objects that the user is able to perceive. The eye tracking sensors can also be used to monitor user's eye fixation, to discount user input when the user was not looking at the specified fixation point while the object(s) being tracked were shown.

Identifying Blind Spots and Measuring a Field of View

Figure 22:
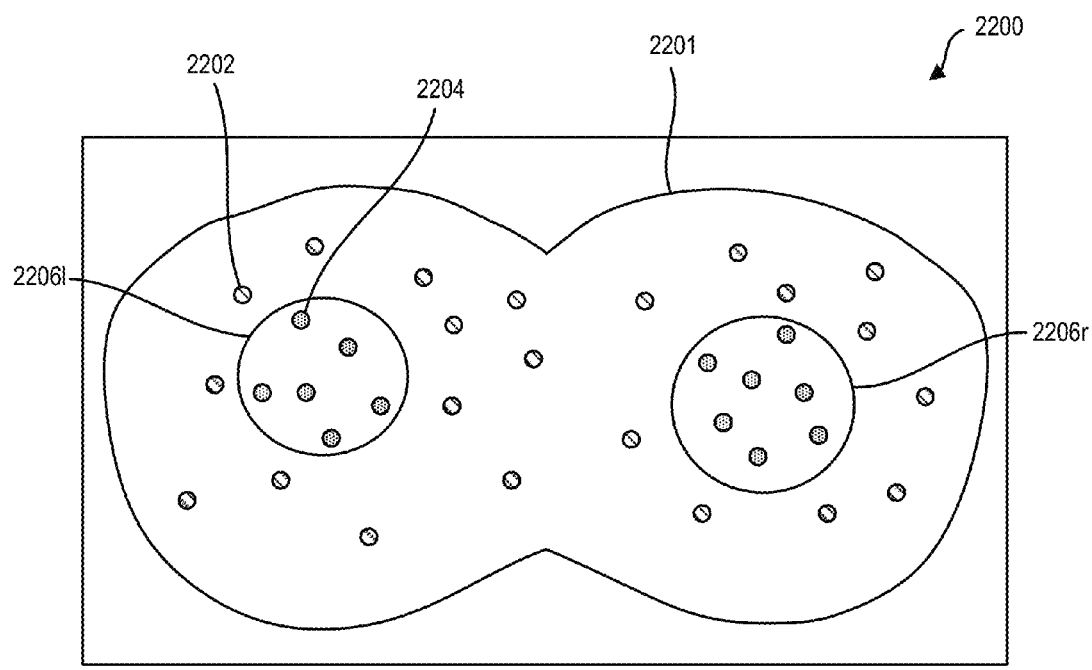
FIG. 22 is a schematic diagram illustrating a 3D map generated as a result of an activity determining user's blind spots.

An activity intended to identify, or map, user's blind spots can be conducted to use with the activity that measures the user's field of view. For example, a scene with target objects can be displayed for a short duration of time (e.g., for a time period in a range from 0.1 seconds to 2 seconds) within the identified user's field of view to one eye at a time. The user is instructed to keep his or her gaze at a fixed point in the scene throughout the activity. Tracked objects can be added to the scene one at a time to the scene at different positions, velocities, sizes, brightness, contrast, color, and movement patterns. By logging which of the displayed tracked objects the user is able to perceive, a map of user's blind spots can be generated. FIG. 22 is a diagram illustrating an exemplary map 2200 including the user's field of view 2201 with tracked objects 2202 that are successfully perceived by the user, tracked objects 2204 that are not perceived by the user, and measured blind spots 2206*l* and 2206*r* in the left and right eyes, respectively.

An activity intended to map user's blind spots can be involve making a guess, or estimating, a location of the user's blind spot based on a typical (normal) location of the blind spot in human subjects. The blind spot is typically located about 12-15° nasal and 1.5° below the horizontal and is roughly 7.5° high and 5.5° wide. The user is instructed to look at a stationary target straight ahead of the user. Objects such as brightly lit, moving targets can be displayed to the user along the outside of a ring centered on the estimated blind spot. Once an object appears on the display, it starts moving toward the center of the estimated blind spot, and the user is instructed to provide input indicating that the user perceived that the spot disappeared, meaning that the estimated blind spot was not estimated correctly. A next blind spot can then be estimated, and the activity is repeated until a center and contours (size) of the user's blind spot are mapped. Stimulus of a different color can be flashed inside the estimated position of the blind spot, and the user can be asked to input when they perceive it, to confirm the measurement of the blind spot is correct.

An activity intended to identify user's blind spots can also involve displaying objects on a 3D scene such that the objects are offset from a fixation point of the eye. Eye tracking sensors can then be used to determine objects that the user is able to perceive. The eye tracking sensors can also be used to monitor user's eye fixation, to discount user input when the user was not looking at the specified fixation point while the object(s) being tracked were shown.

Color Perception

Measuring Color Perception

An activity intended to measure user's color perception can include displaying to the user a set of images representing Ishihara plates used to conduct a color perception test for red-green color deficiencies. The user can be instructed to indicate which number/letter the user can see.

Figure 23:
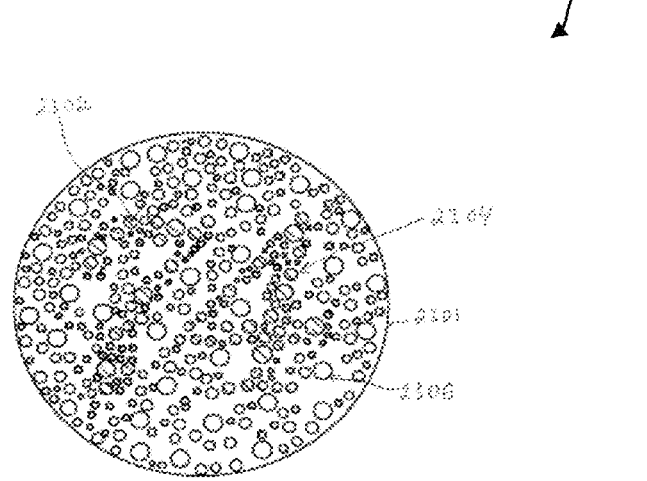
FIG. 23 is a schematic diagram illustrating an image presented to at least one of the left and right eyes of the user during an activity to measure user's color perception.

An activity intended to measure user's color perception can include displaying to the user a scene with a background of a certain color, or groups of colors (background hues). After the scene with the colored background is displayed, one or more colored target objects can be displayed on the scene at certain time intervals. The time intervals can be selected randomly or in other manner. The user is instructed to interact with the displayed objects as they appear on the scene using a suitable input device, e.g., a mouse, keyboard, gamepad controller, a head-mounted VR device, or any other input device. Information on the hues of the objects the user interacts with is recorded and then used to calculate a measurement of the user's color perception. FIG. 23 illustrates a scene 2300 including an image 2301 of an Ishihara plate that can be displayed during an activity intended to measure user's color perception. The image 2301 of the Ishihara plate (which is displayed in color) includes a number "74" formed by the patterned dots and that should be clearly visible to viewers with normal color vision and invisible, or difficult to see, to people with a red-green color vision defect. As shown in FIG. 23, the image 2301 has a target object 2302 in the form of number "7" and a target object 2304 in the form of number "4." The rest of the dots within the image 2301 of the Ishihara plate are collectively denoted as a background 2306. It should be appreciated that the Ishihara plate can include other numbers or various shapes. More than one image of different Ishihara plates can be rendered for a user to view to measure user's color perception.

An activity intended to measure user's color perception can also include displaying a set of objects of colors generated along a gradient from color A to color B. For example, objects of the color A can be disposed leftmost within the set and objects of the color B as can be disposed rightmost within the set. The objects can then be shuffled randomly and the shuffled set can be displayed to the user along with or without the original set.

Figure 24:
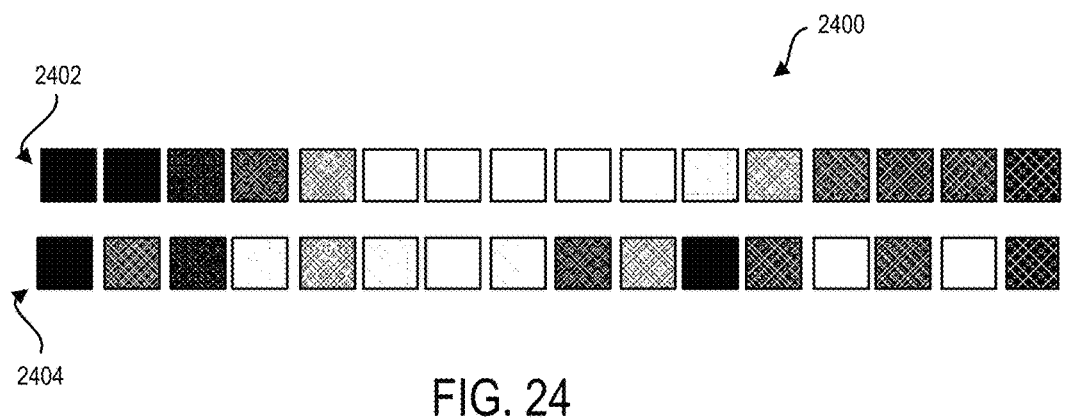
FIG. 24 is another schematic diagram illustrating an image presented to at least one of the left and right eyes of the user during an activity to measure user's color perception.

FIG. 24 is a diagram 2400 that can be displayed during an activity intended to measure user's color perception. The diagram 2400 includes a first set of colors 2402 where square objects are arranged along a gradient from color A (left) to color B (right). The colors A, B, can be, for example, red and green. However, other colors can be used as well. A second set 2404 includes the square objects of the first set 2402 randomized. The user can be instructed to arrange the objects in the second set 2404 in accordance with their original order as shown in the first set 2402. It should be appreciated that sixteen square objects are shown in each set by way of example only, as any suitable number of any types of objects can be presented to the user measure user's color perception.

Measuring Color Fatigue

Figure 25A:
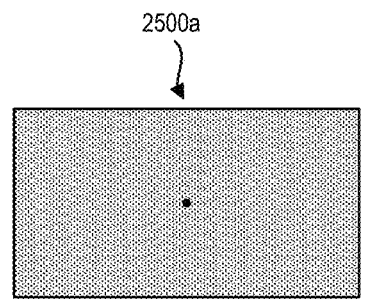
FIG. 25A is a schematic diagram illustrating an image presented to at least one of the left and right eyes of the user during an activity to measure color fatigue.
Figure 25B:
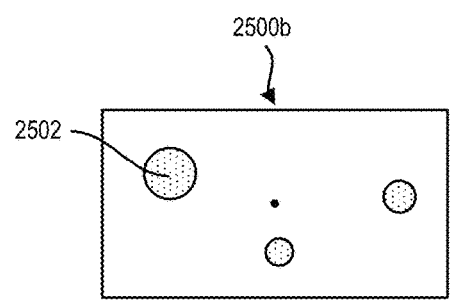
FIG. 25B is another schematic diagram illustrating an image presented to at least one of the left and right eyes of the user during an activity to measure color fatigue.

An activity intended to measure user's color fatigue can include displaying an image of a solid color (fatigue color) to both eyes for a certain time period. The scene is then modified to add to it one or more targets objects having a color that is a faded version of a color complementary to the fatigue color. The user is instructed to look at the objects to "interact" with them. FIG. 25A illustrates an initial scene 2500*a* having a fatigue color, and FIG. 25B illustrates an interaction scene 2500*b* having objects 2502 of a color complementary to the fatigue color. The fatigue color can be, for example, a blue color, and a color complementary to the fatigue color can be, for example, an orange color.

Adjusting for Color Blindness

An activity intended to measure user's color blindness can include adjusting colors of all objects within the scene and colors of the scene itself to compensate for user's color blindness, making the contrast of the colors in the scene look more like what a person with normal color sensitivity would see. The color blindness can thus be measured following measuring the user's sensitivity to a particular color.

Displaying Impossible Colors

An activity intended to correct user's color perception can include displaying images of an object different hues to each eye such that the images are overlaid in the same scene and the user's brain is able to perceive the object to be a color that the user could not otherwise see (e.g., under normal conditions).

Measuring Contrast Sensitivity

An activity intended to measure user's contrast sensitivity can include adjusting a plurality of objects against a black background. The user can be instructed to interact with each object in the scene to "destroy" the object such that the object is no longer displayed. The objects can be removed from the scene once the user looks at that object, which can be detected using head tracking and/or eye tracking sensor technology. Various properties of the object, such as a contrast, brightness, color, saturation, movement pattern, and other properties, can be adjusted automatically or in response to respective user input. The information relating to objects and the properties of the objects that the user can perceive can be recorded.

An activity intended to measure user's contrast sensitivity can include displaying Snellen letters with crowding bars at a certain contrast. A size of the Snellen letters against the background can be modified automatically or in response to respective user input (e.g., input received from the user being tested or from a clinician controlling the testing process), and a threshold size can be determined at which the user can no longer correctly identify the letter. The activity can be conducted for each eye separately as well as for both eyes in a random order.

Figure 26:
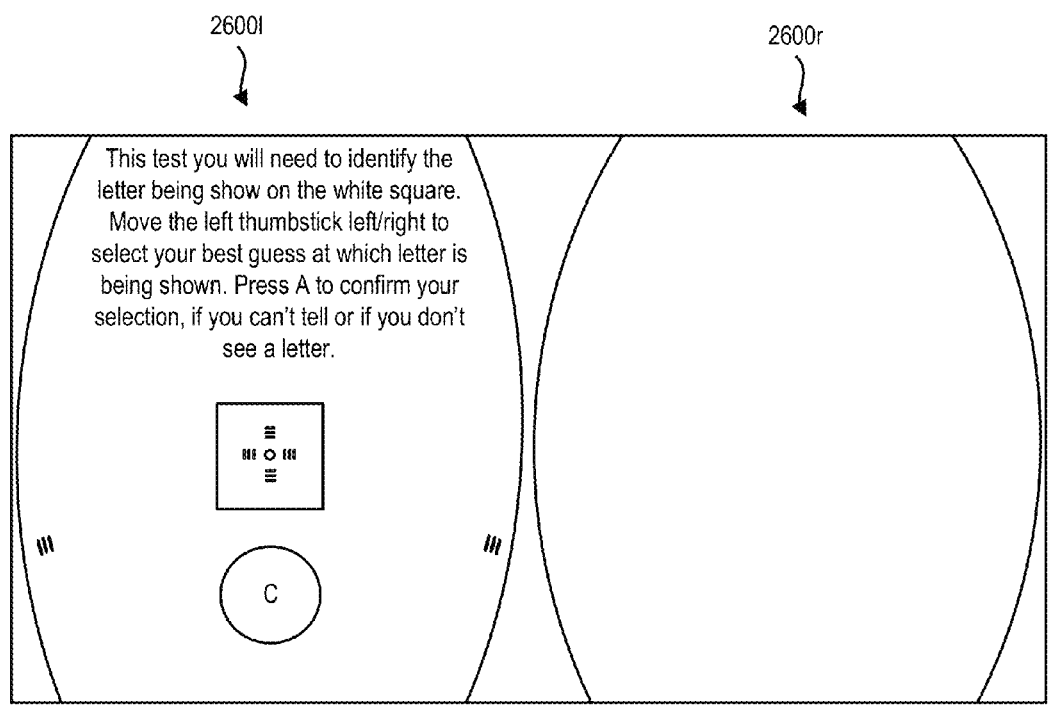
FIG. 26 is a schematic diagram illustrating images presented to the left and right eyes of the user during an activity to measure user's contrast sensitivity.

An activity intended to measure user's contrast sensitivity can include displaying Snellen letters with crowding bars at a certain spatial frequency. A brightness of the Snellen letters against the background can be modified automatically or in response to respective user input (e.g., input received from the user being tested or from a clinician controlling the testing process), and a threshold size can be determined at which the user can no longer correctly identify the letter. The activity can be conducted for each eye separately as well as for both eyes in a random order. FIG. 26 illustrates an example of an image 2600*l* and an image 2600*r* that can be displayed to the left and right eyes of the user, respectively, to measure user's contrast sensitivity. The letter in the center is intended to be identified by the viewer's left eye alone, while the lines surrounding it, the crowding bars, make it more difficult to identify than if it were alone.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. A computer system for vision assessment and correction, the system comprising:
   a computing device comprising at least one data processor and at least one computer-readable storage medium storing computer-executable instructions; and
   a head-mountable virtual reality device configured to communicate with the computing device and having a virtual reality display configured to render a virtual reality environment;
   wherein the at least one data processor is configured to execute the computer-executable instructions to perform:
      displaying, using the at least one data processor and on the virtual reality display, the virtual reality environment comprising a first object having a first property, the first object being displayed to a user wearing the head-mountable virtual reality device during an eye condition assessment or correction activity;
      receiving, by the at least one data processor, user input with respect to the first object, the user input being generated based on input acquired from the user during the eye condition assessment or correction activity;
      tracking movements of a head of the user during the eye condition assessment or correction activity;
      determining, by the at least one data processor using the received user input, whether a target value of at least one parameter has been reached, wherein the target value of the at least one parameter is indicative of a perception of the first property of the first object by at least one eye of the user;
      when it is determined that the target value has not been reached, displaying, using the at least one data processor and on the virtual reality display, the virtual reality environment comprising a second object having a second property that is different from the first property, the second object being generated based at least in part on a result of the tracking the movements of the head of the user; and
      iteratively performing the displaying, receiving, tracking, and determining steps until it is determined that the target value has been reached.

2. The computer system of claim 1, wherein:
   the second object comprises a modified representation of the first object.

3. The computer system of claim 1, wherein:
   the user input is received from at least one input device selected from the group consisting of a mouse, a keyboard, a gesture and motion tracking device, a microphone, at least one camera, an omnidirectional treadmill, and a game pad.

4. The computer system of claim 1, wherein:
   the user input is received from at least one sensor selected from the group consisting of a head tracking sensor, a face tracking sensor, a hand tracking sensor, an eye tracking sensor, a body tracking sensor, a voice recognition sensor, a heart rate sensor, a skin capacitance sensor, an electrocardiogram sensor, a brain activity sensor, a geolocation sensor, at least one retinal camera, a balance tracking sensor, a body temperature sensor, a blood pressure monitor, and a respiratory rate monitor.

5. The computer system of claim 1, wherein:
   the computing system comprises a mobile computing device.

6. The computer system of claim 1, wherein:
   information displayed by the head-mountable virtual reality device is controlled via a second computing device.

7. The computer system of claim 1, wherein the at least one data processor is further configured to execute the computer-executable instructions to:
   determine that the target value of the at least one parameter has been reached; and
   when it is determined that the target value has been reached, provide a result relating to the eye condition assessment or correction activity.

8. The computer system of claim 7, wherein the result comprises at least one selected from the group consisting of a determination of depth perception, an identification of a dominant eye, information relating to breaking interocular suppression of an amblyopic eye, a measurement of an interpupillary distance, and information relating to strengthening a weak eye.

9. The computer system of claim 1, wherein the second property of the second object that is different from the first property of the first object comprises intensity.

10. The computer system of claim 1, wherein the target value of the at least one parameter comprises at least one numerical value at which the eye condition assessment or correction activity is determined to be completed.

11. The computer system of claim 1, wherein the at least one data processor is configured to execute the computer-executable instructions to perform:
   determining at least one numerical value of the at least one parameter representing the perception of the first property of the first object by the at least one eye of the user; and
   comparing the determined numerical value to the target value.

12. The computer system of claim 1, wherein the second object is generated based on user input comprising an instruction to the at least one data processor to modify the first property of the first object.

13. The computer system of claim 1, wherein the second object is generated by randomly modifying the first property of the first object.

14. The computer system of claim 1, wherein determining, by the at least one data processor using the received user input, that the target value of the at least one parameter has not been reached comprises receiving an indication that the user was not able to perceive the first object in accordance with at least one requirement of the eye condition assessment or correction activity.

\* \* \* \* \*